(12) United States Patent
Abbate et al.

(10) Patent No.: US 10,343,985 B2
(45) Date of Patent: Jul. 9, 2019

(54) CRYOPYRIN INHIBITORS FOR PREVENTING AND TREATING INFLAMMATION

(71) Applicant: VIRGINIA COMMONWEALTH UNIVERSITY, Richmond, VA (US)

(72) Inventors: Antonio Abbate, Richmond, VA (US); Shijun Zhang, Richmond, VA (US); Benjamin Van Tassell, Richmond, VA (US)

(73) Assignee: VIRGINIA COMMONWEALTH UNIVERSITY, Richmond, VA (US)

( * ) Notice: Subject to any disclaimer, the term of this patent is extended or adjusted under 35 U.S.C. 154(b) by 54 days.

(21) Appl. No.: 14/928,450

(22) Filed: Oct. 30, 2015

(65) Prior Publication Data

US 2016/0052876 A1  Feb. 25, 2016

Related U.S. Application Data

(63) Continuation-in-part of application No. PCT/US2014/038913, filed on May 21, 2014.

(60) Provisional application No. 61/901,187, filed on Nov. 7, 2013, provisional application No. 61/825,623, filed on May 21, 2013.

(51) Int. Cl.
   *C07C 311/37* (2006.01)
   *C07C 311/46* (2006.01)
   *C07C 311/49* (2006.01)

(52) U.S. Cl.
   CPC .......... *C07C 311/37* (2013.01); *C07C 311/46* (2013.01); *C07C 311/49* (2013.01)

(58) Field of Classification Search
   None
   See application file for complete search history.

(56) References Cited

U.S. PATENT DOCUMENTS

| | | |
|---|---|---|
| 3,454,635 A | 7/1969 | Weber et al. |
| 3,489,798 A | 1/1970 | Weber et al. |
| 3,621,057 A | 11/1971 | Weber et al. |
| 3,917,690 A | 11/1975 | Weber et al. |
| 3,932,503 A | 1/1976 | Weber et al. |
| 2009/0016354 A1 | 1/2009 | Isobe |

FOREIGN PATENT DOCUMENTS

| | | |
|---|---|---|
| GB | 1212695 | 11/1970 |
| WO | 2009043784 A1 | 4/2009 |
| WO | 2013/007763 A1 | 1/2013 |

OTHER PUBLICATIONS

Lipinski et al., J. Cardiovasc. Pharmacol., vol. 63, No. 4, Apr. 2014.*
Ito et al. In Cancer Science 94(1), 3-8 (2003).*
STN Registry Database entry for CAS RN 1385981-32-7, Entry Date Aug. 3, 2012, Accessed Jun. 12, 2018.*
STN Registry Database entry for CAS RN 16673-34-0, Entry Date Nov. 16, 1984, Accessed Aug. 28, 2018.*
STN Registry Database entry for CAS RN 1092043-61-2, Entry Date Dec. 30, 2008, Accessed Jan. 31, 2019.*
Hsi, "Synthesis of Carbon-14 and Tritium Labeled Glyburide", Journal of Labelled Compounds, 1973, 9(1):91-105.
Biere et al, "Blood Glucose Lowering Sulfonamides with Asymmetric Carbon Atoms", Journal of Medical Chemistry, 1974, 17(7):716-721.
Masereel et al., "Synthesis and Biological Evaluation of Sulfonylcyanoguanidines and Sulfonamidonitroethylenes as Bioisosteres of Hypoglycemic Sulfonylureas", European Journal of Medical Chemistry, 1997, 32:453-456.
Masereel et al., "First Synthesis of 4-Substituted Benzenesulfonylcyanoguanidines", Tetrahedron Letters, 1996, 37(40):7253-7254.
Schmitz et al., "Synthesis and Evaluation of Fluorine-18 Labeled Glyburide Analogs as beta-Cell Imaging Agents", Nuclear Medicine and Biology, 2004, 32:483-491.
Lamkanfi et al., "Glyburide inhibits the Cryopyrin/Nalp3 inflammasome", J Cell Biol, 2009, vol. 187, No. 1, pp. 61-70.
Grishman et al., "Toll-like receptors, the NLRP3 inflammasome, and interleukin-1[beta] in the development and progression of type 1 diabetes", Pediatric Research, 2012, vol. 71, No. 6, pp. 626-632.
Marchetti et al., "A novel pharmacologic inhibitor of the NLRP3 inflammasome limits myocardial injury after ischemia-reperfusion in the mouse", J Cardiovasc Pharmacol, Apr. 2014, vol. 63, No. 4, pp. 316-322.

* cited by examiner

*Primary Examiner* — Alicia L Otton
(74) *Attorney, Agent, or Firm* — W & C IP

(57) ABSTRACT

Inhibitors that are anti-inflammatory agents are provided, as are methods of using the analogs to inhibit inflammation and prevent or treat diseases and conditions associated with inflammation, such as heart failure and autoimmune diseases.

2 Claims, 17 Drawing Sheets

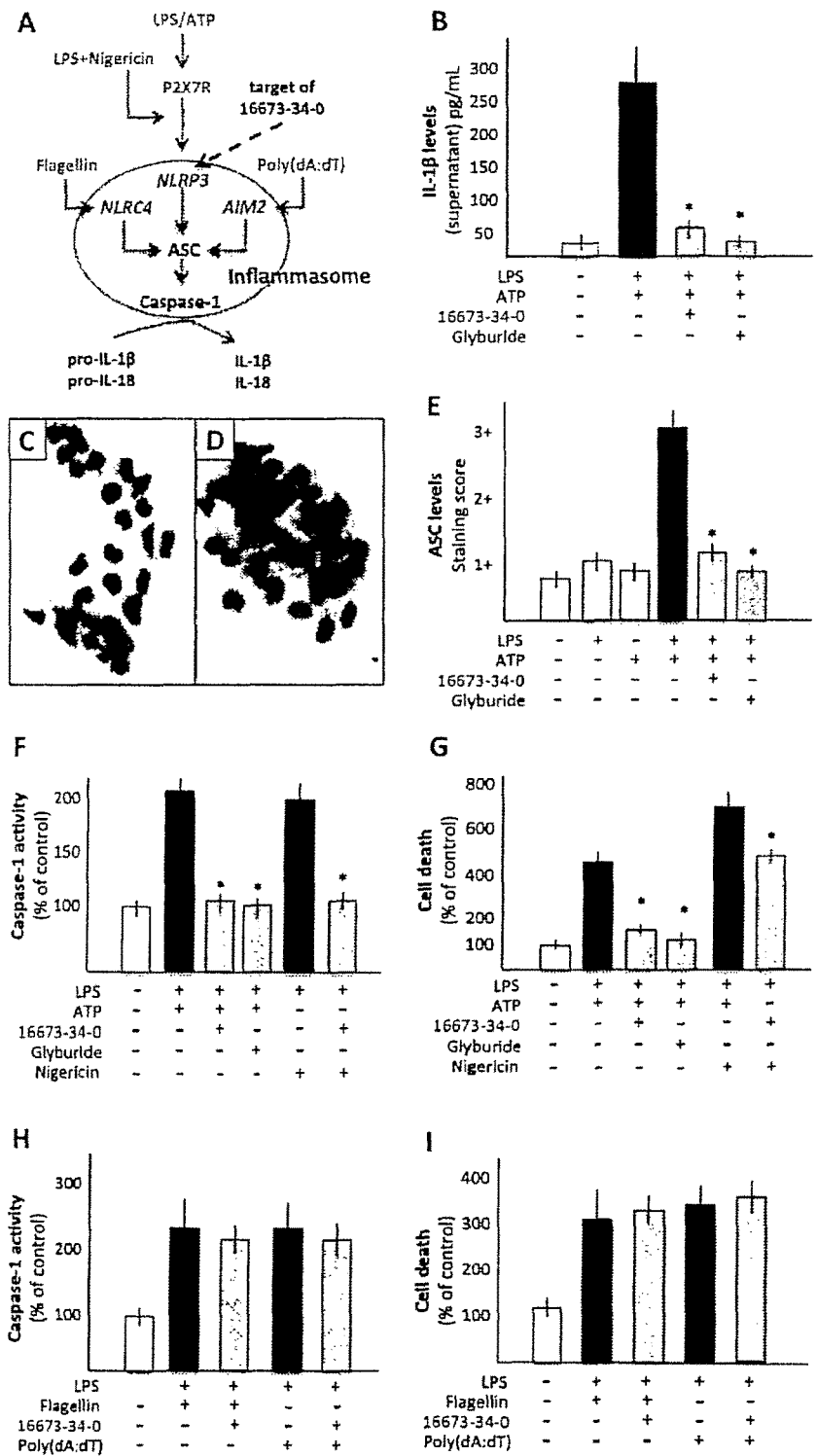
Figure 4A-I

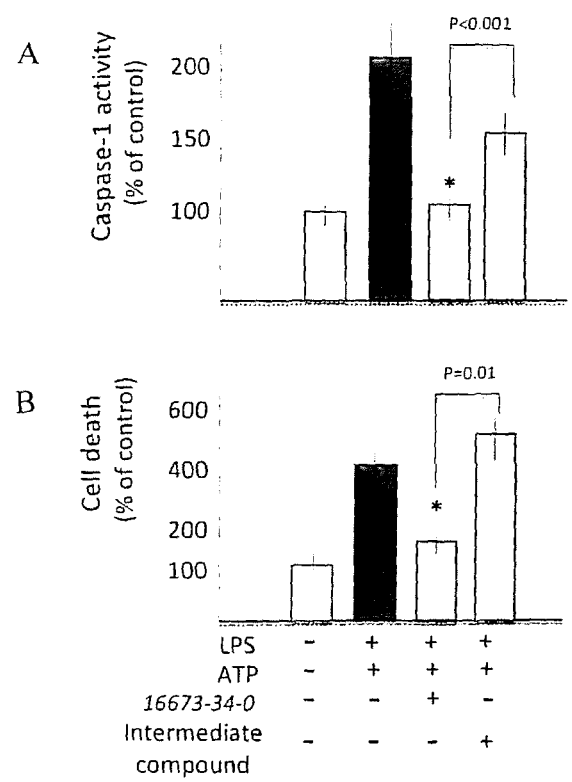
Figure 5A and B

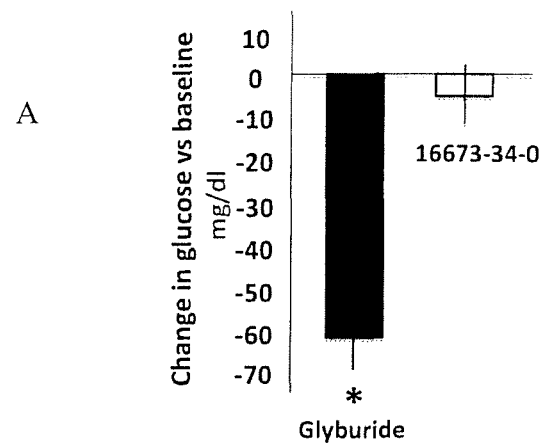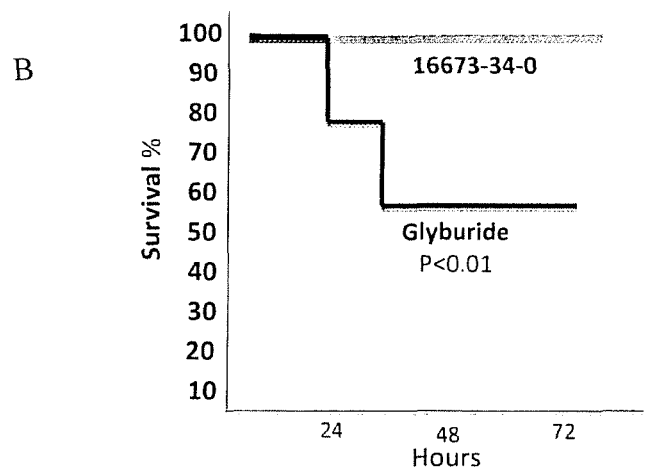
Figure 6A and B

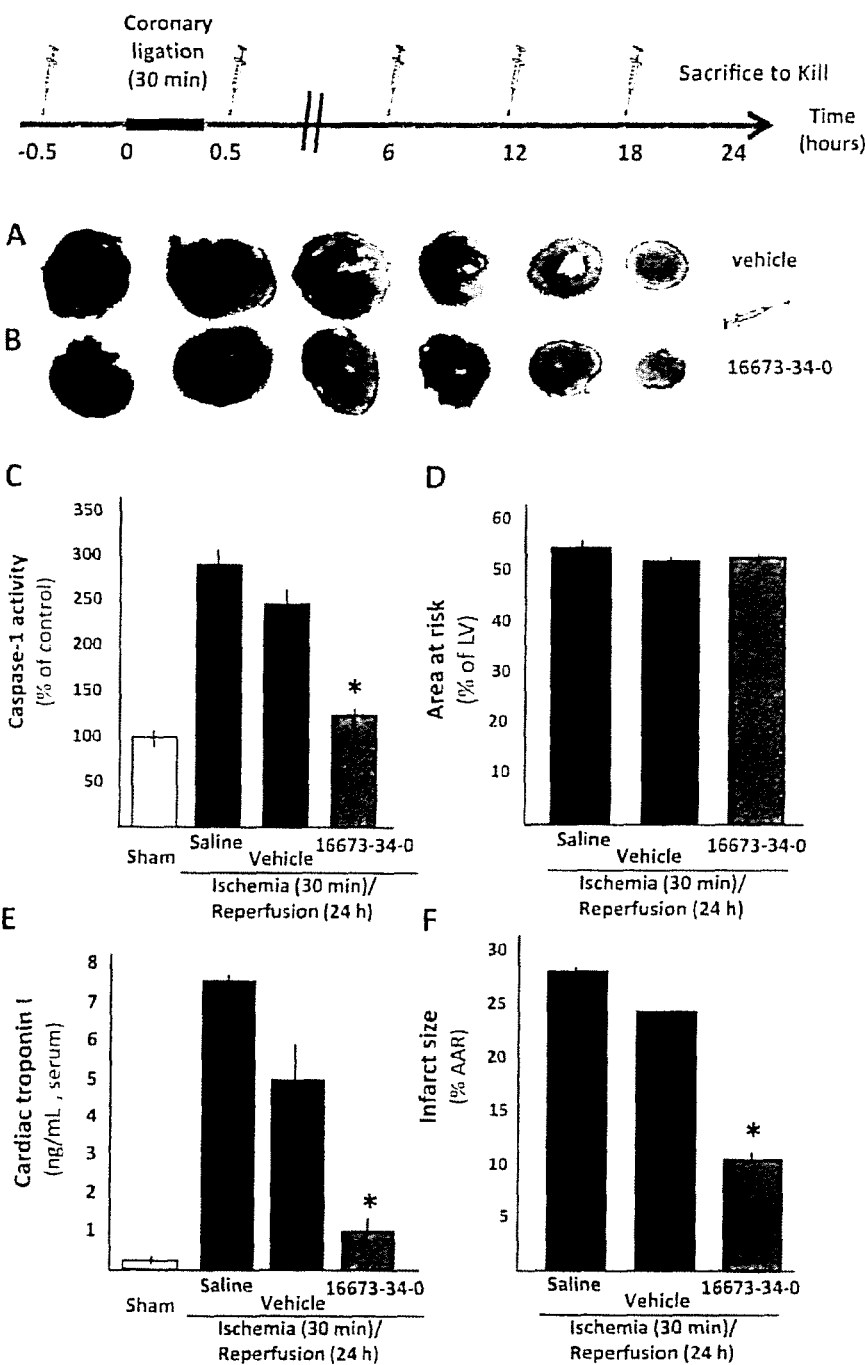
Figure 7A-F

Figure 9A and B

Figure 10A and B

Figure 13A and B

A.
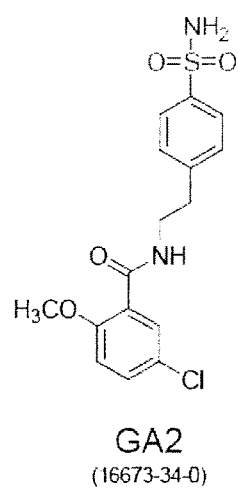
GA2
(16673-34-0)
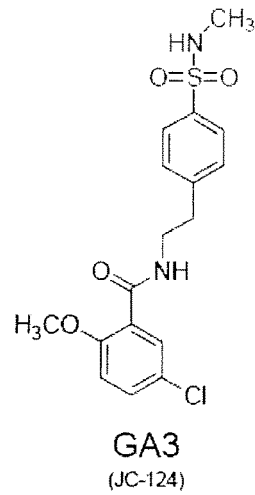
GA3
(JC-124)
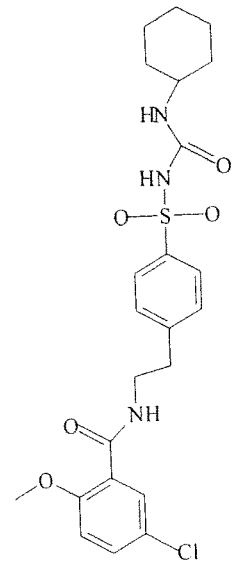
Glyburide
(GLY)
B.
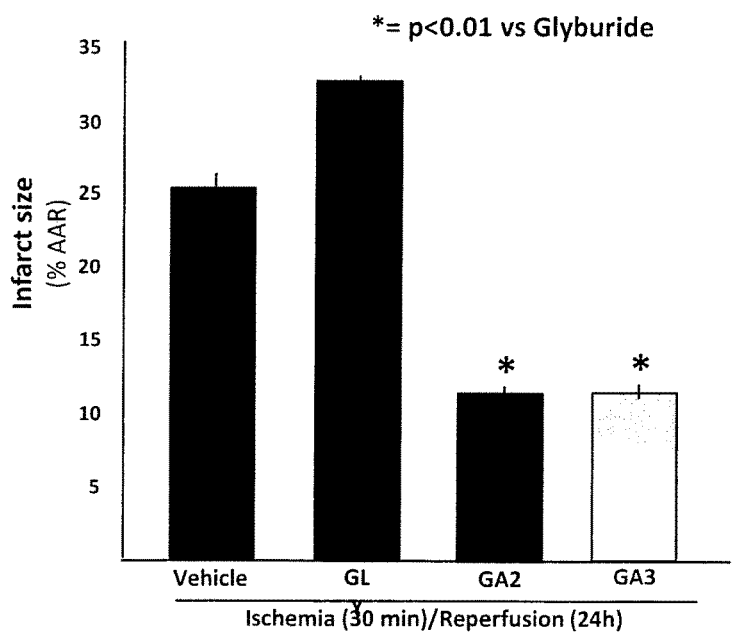
Figure 15A and B A.
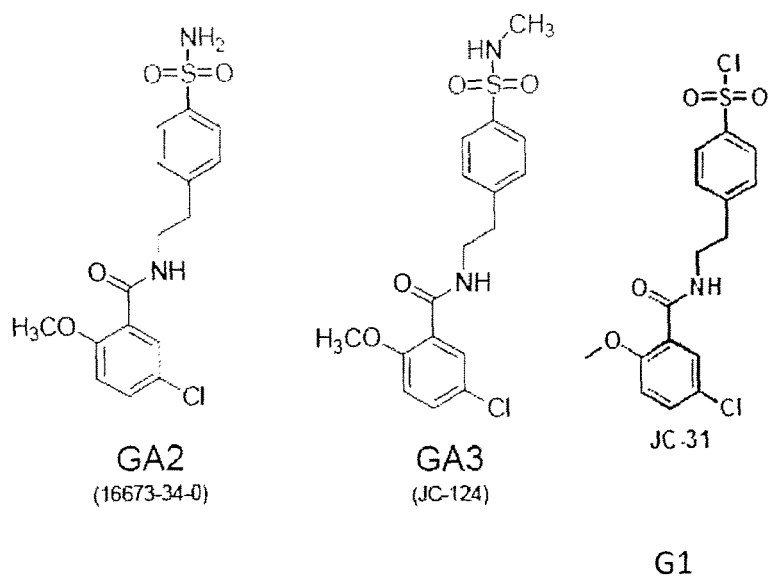
B.
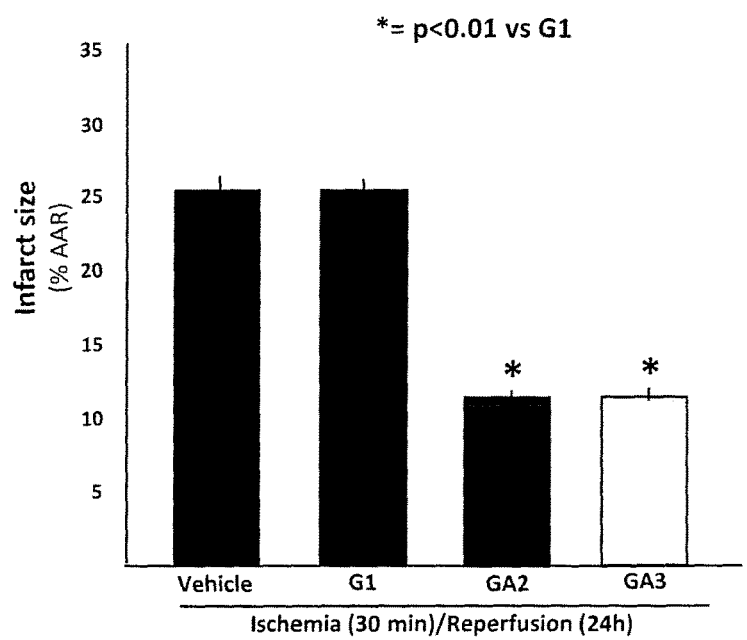
Figure 16A and B

CRYOPYRIN INHIBITORS FOR PREVENTING AND TREATING INFLAMMATION

BACKGROUND OF THE INVENTION

Field of the Invention

The invention generally relates to improved anti-inflammatory agents and methods of their use to inhibit inflammation. In particular, the invention provides compounds that inhibit cryopyrin (NRLP3 or NALP3) inflammasome formation and activation, and methods of using the analogs to prevent or treat NRLP3 inflammasome associated diseases and conditions, such as heart failure and acute and chronic inflammatory diseases.

Background of the Invention

Inflammasomes are protein complexes that recognize a diverse set of inflammation-inducing stimuli and control the production of important pro-inflammatory cytokines such as IL-1β and IL-18 through the activation of caspase-1. All inflammasomes share a similar structure and are typically formed by a NOD-like receptor (NLR) sensor component (i.e. cryopyrin [NLRP3 or NALP3]), an adaptor component (ASC), an effector component (caspase-1) and the substrate component (the pro-inflammatory cytokines pro-IL-1β and pro-IL-18). The sensors recognize danger signals such as Damage associated molecular pattern molecules (DAMPs) released during tissue injury or stress (extracellular ATP, urate crystal, β-amyloid, cell debris) and Pathogen-associated molecular patterns (PAMPs), evolutionary conserved structures of infectious pathogens. Among the NLR family members, cryopyrin (NLRP3 or NALP3) is the most studied inflammasome sensor. The assembly of the inflammasome requires the interaction of the pyrin domains of cryopyrin and the adaptor component ASC (apoptosis-associated speck-like protein containing a caspase recruitment domain). This interaction leads to the recruitment of caspase-1 and subsequently to maturation and secretion of pro-inflammatory cytokines IL-β and IL-18. Through this complex interaction between the sensors, adaptors, and effectors, the inflammasome serves as a "guardian" for external or internal stress and a key "amplifier" of the inflammatory response.

Acute myocardial infarction (AMI) refers to a clinical syndrome in which heart cells die due to ischemia, an imbalance between oxygen supply and demand. AMI is among the most frequent causes of adverse cardiac remodeling, heart failure, and death worldwide. The death of heart cells during AMI leads to an initial loss of functional heart muscle (myocardium) which is followed by a second wave of injury mediated by the sterile inflammatory response. The inflammasome occupies a central role in the inflammatory response following ischemic injury such as AMI. The degree of the inflammatory response during AMI predicts the clinical outcome in patients with AMI, with those patients having more inflammation showing higher rates of heart failure or death. Recent studies have shown that inhibition of the formation of the inflammasome in experimental AMI using small interfering (silencing) RNA directed toward the sensor, cryopyrin, leads to reduced cardiac injury and more favorable infarct healing (Mezzaroma et al, Proc Natl Acad Sci 2011; 127:143-152). Similar effects were seen in the mouse knock-out for ASC (a scaffolding protein for the inflammasome). These data indicate a central role of cryopyrin in the formation of inflammasomes in the heart during AMI, and the potential value of cryopyrin inhibition to prevent adverse cardiac remodeling after AMI. There are no known drugs specifically targeted to inhibit cryopyrin.

Glyburide, an anti-diabetic drug promoting insulin release from pancreatic β-cells, has been shown to have inhibitory activity on cryopyrin in myeloid cells in vitro. In addition, some observational studies suggest that glyburide also has a protective anti-inflammatory effect in patients. However, the use of glyburide as an effective anti-inflammatory treatment in vivo is limited by the need for very high doses which cause severe, potentially lethal, hypoglycemia. Moreover, glyburide has also shown to be potentially "cardiotoxic" due to its ability to limit ischemic preconditioning, an innate protective effect.

There is an urgent need for new therapeutic strategies specifically aimed at modulating inflammation, for example, sterile inflammation associated with AMI. The current approach of reperfusion and inhibition of neurohormonal activation has successfully reduced morbidity and mortality of AMI, but AMI is still associated with unacceptably high incidence of heart failure and death related to the excessive unopposed inflammatory activity.

SUMMARY OF THE INVENTION

The sulfonyl and the benzamide moieties of glyburide are involved in inhibition of cryopyrin, whereas the cyclohexylurea moiety is involved in insulin release and ischemic preconditioning. The presence of the cyclohexylurea moiety characterizes the class of drugs known as sulfonylureas. A new family of analogs has been designed that retains the sulfonyl and the benzamide moieties but that is free of the cyclohexylurea portion of glyburide, i.e. the cyclohexylurea portion is not present, and thus not part of the sulfonylureas used to treat diabetes. The resulting compounds inhibit the formation and activity of the cryopyrin (NRLP3, NALP3) inflammasome, thus acting as anti-inflammatory agents, without affecting insulin release or ischemic preconditioning. Accordingly, the present disclosure provides novel analogs that are anti-inflammatory agents, and methods of their use to inhibit inflammation, e.g. by inhibiting cryopyrin (NRLP3) inflammasome formation and/or activity. In some aspects, the agents and methods are used for the treatment of AMI, e.g. in order to prevent or treat heart failure associated with inflammation, both initial inflammation and the "second wave" of inflammation that occurs after AMI. In other aspects, the inhibitors are used to prevent or treat other NRLP3 inflammasome-mediated diseases such as gout and various auto-inflammatory diseases. The inhibitors are advantageously non-toxic when administered in vivo.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

It is an object of this invention to provide a compound of Formula I:

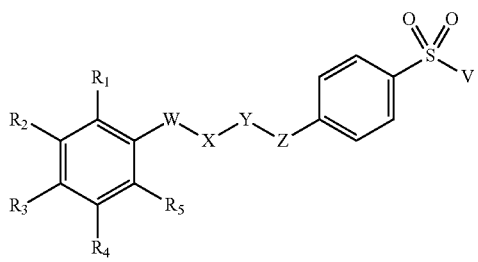

Formula I wherein

R1 is unbranched, branched, saturated, unsaturated, cyclic or acyclic, substituted or unsubstituted C1-C8 alkyl or is unbranched, branched, saturated, unsaturated, cyclic or acyclic, substituted or unsubstituted C1-C8 alkoxyl;

R4 is halogen, amino, nitro or cyano;

R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;

W is unbranched, branched, saturated, unsaturated, substituted or unsubstituted C1-C4 alkyl and may be present or absent;

X is carbonyl or $CH_2$ or $CH_2OH$; and

Y is NH, O, or S; and

Z is C1-C5 unbranched, branched, saturated, unsaturated, cyclic or acyclic, substituted or unsubstituted alkyl, or NHR wherein R is selected from C1-C5 unbranched, branched, saturated, unsaturated, cyclic or acyclic, substituted or unsubstituted alkyl V is i) $NR^1R^2$ where $R^1$ and $R^2$ are H or $C_1$-$C_6$ alkyl and may be the same or different; or ii) a saturated heterocycle comprising N bonded directly to S; or iii) an unsubstituted or substituted guanidine moiety; and pharmaceutically acceptable salts thereof. In one aspect, the compound is

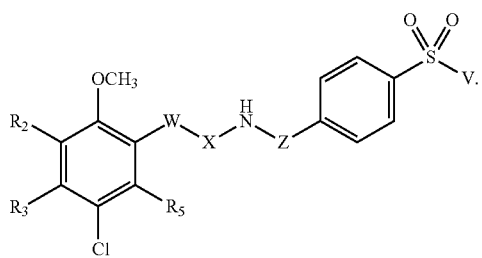

Formula II

In another aspect, the compound is

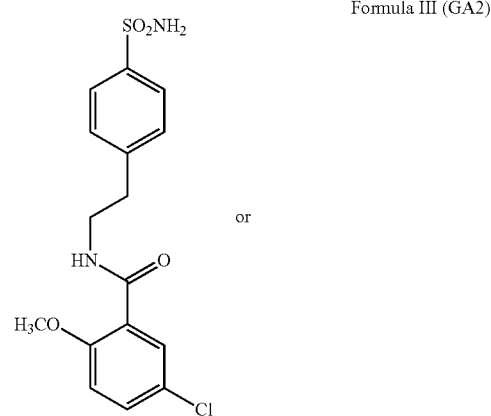

Formula III (GA2)

or

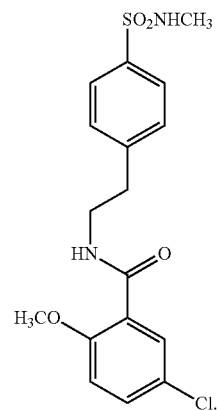

Formula IV (GA3)

The invention also provides compositions comprising each of these compounds, and variants thereof as described herein, combined with a physiologically acceptable carrier.

The invention also provides methods of preventing or treating NRLP3 inflammasome-associated inflammation in a subject in need thereof, comprising a step of administering to said subject a therapeutically effective amount of the compound of Formula

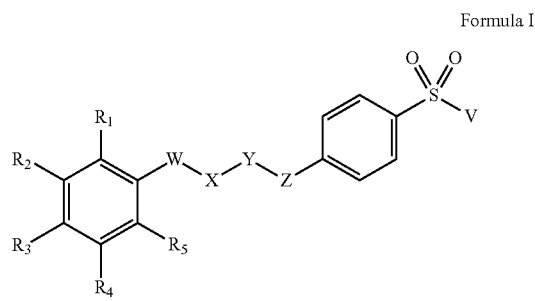

Formula I wherein

R1 is unbranched, branched, saturated, unsaturated, cyclic or acyclic, substituted or unsubstituted C1-C8 alkyl or is unbranched, branched, saturated, unsaturated, cyclic or acyclic, substituted or unsubstituted C1-C8 alkoxyl;

R4 is halogen, amino, nitro or cyano;

R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;

W is unbranched, branched, saturated, unsaturated, substituted or unsubstituted C1-C4 alkyl and may be present or absent;

X is carbonyl or CH$_2$ or CH$_2$OH; and

Y is NH, O, or S; and

Z is C1-C5 unbranched, branched, saturated, unsaturated, cyclic or acyclic, substituted or unsubstituted alkyl, or NHR wherein R is selected from C1-C5 unbranched, branched, saturated, unsaturated, cyclic or acyclic, substituted or unsubstituted alkyl V is i) NR$^1$R$^2$ where R$^1$ and R$^2$ are H or C$_1$-C$_6$ alkyl and may be the same or different; or ii) a saturated heterocycle comprising N bonded directly to S; or iii) an unsubstituted or substituted guanidine moiety. In some aspects of the methods, the compound is Formula II In other aspects of the methods, the compound is Formula III (GA2)

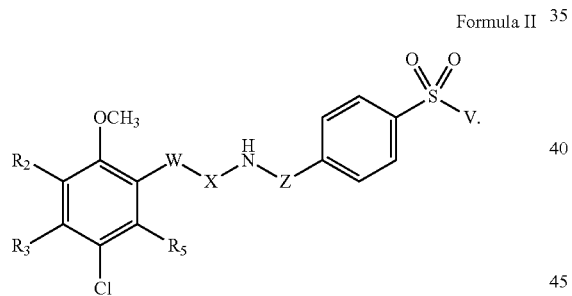

or

Formula IV (GA3)

In exemplary methods, the NRLP3 inflammasome-associated inflammation is selected from the group consisting of adverse cardiac remodeling after acute myocardial infarction (AMI); peritonitis, and an autoinflammatory condition.

The invention also provides methods of preventing or treating heart failure in a subject who has had an acute myocardial infarction (AMI), comprising a step of administering to said subject a therapeutically effective amount of the compound of Formula I:

Formula I wherein

R1 is unbranched, branched, saturated, unsaturated, cyclic or acyclic, substituted or unsubstituted C1-C8 alkyl or is unbranched, branched, saturated, unsaturated, cyclic or acyclic, substituted or unsubstituted C1-C8 alkoxyl;

R4 is halogen, amino, nitro or cyano;

R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;

W is unbranched, branched, saturated, unsaturated, substituted or unsubstituted C1-C4 alkyl and may be present or absent;

X is carbonyl or CH$_2$ or CH$_2$OH; and

Y is NH, O, or S; and

Z is C1-C5 unbranched, branched, saturated, unsaturated, cyclic or acyclic, substituted or unsubstituted alkyl, or NHR wherein R is selected from C1-C5 unbranched, branched, saturated, unsaturated, cyclic or acyclic, substituted or unsubstituted alkyl V is i) $NR^1R^2$ where $R^1$ and $R^2$ are H or $C_1$-$C_6$ alkyl and may be the same or different; or ii) a saturated heterocycle comprising N bonded directly to S; or iii) an unsubstituted or substituted guanidine moiety.

In exemplary methods, the compound is

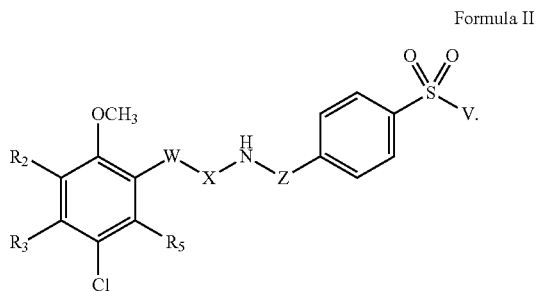

Formula II

In additional exemplary methods, the compound is

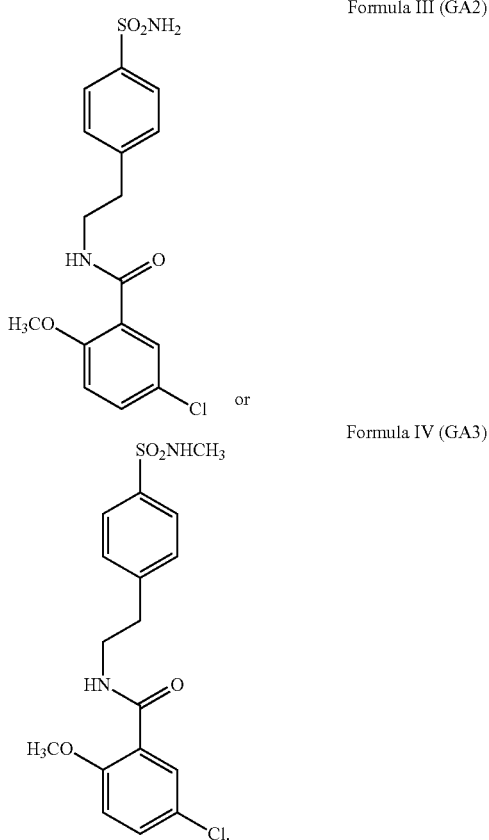

Formula III (GA2)

or

Formula IV (GA3)

BRIEF DESCRIPTION OF THE DRAWINGS

FIG. 4A-I. Targeted inhibition of the NLRP3 inflammasome by 16673-34-0.

Figure 1:
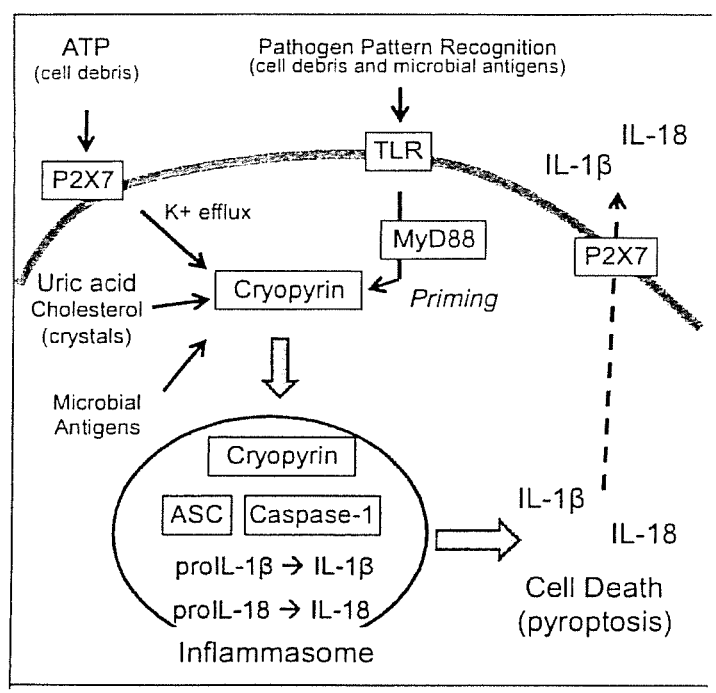
FIG. 1. Simplified scheme of cryopyrin activation and inflammasome formation, leading to amplification of the inflammatory response (IL-1β and IL-18), and promoting cell death (pyroptosis).

Panel A shows a schematic representation of the stimuli for the formation of the NLRP3 inflammasome and the NLRC4 and AIM2 inflammasomes. Panel B shows increased interleukin-1β (IL-1β) release by cultured macrophages (J774A.1) in response to LPS/ATP, which is inhibited by 16673-34-0 or glyburide (*P<0.05 vs LPS/ATP). Panels C-E show ASC aggregation in cardiomyocytes in culture (HL-1) without stimulation (panel C) or following LPS/ATP (panel D), with a quantification in panel E showing inhibition of ASC aggregate formation following LPS/ATP by treatment with 16673-34-0 or glyburide (*P<0.05 vs LPS/ATP). Panels F and G show increased caspase-1 activity and cell death following LPS/ATP or LPS/nigericin in cardiomyocytes, also prevented by treatment with 16673-34-0 or glyburide (*P<0.05 vs LPS/ATP or LPS/Nigericin). Panels H and I show an increase in caspase-1 activity and cell death, respectively, following stimulation of the NLRC4 or AIM2 inflammasomes with flagellin or Poly(dA:dT), respectively, and a lack of inhibitory effect by 16673-34-0.

FIGS. 5A and B. An 16673-34-0 intermediate lacking the sulfonyl residue has no inhibitory effects on the NLRP3 inflammasome. The figures show increased caspase-1 activity (A) and cell death (B) following LPS/ATP in cardiomyocytes, prevented by treatment with 16673-34-0 but not by an intermediate compound in the synthesis which lacks the sulfonyl residue (*P<0.05 vs LPS/ATP). P values between 16673-34-0 and intermediate compound are shown in the figure.

FIGS. 6A and B. 16673-34-0 has no effects on glucose control in the mouse in vivo. Panel A shows a lack of significant changes in glucose levels 2 hours after a single dose of 16673-34-0 (100 mg/kg) and a significant reduction after glyburide 132.5 mg (equimolar to 16673-34-0 100 mg/kg). Panel B shows a 50% mortality in healthy mice treated with glyburide 132.5 mg every 6 hours for 24 hours, and lack of any effects of 16673-34-0 100 mg/kg every 6 hours for 24 hours (P<0.01).

FIG. 7A-F. 16673-34-0 inhibits the NLRP3 inflammasome in acute myocardial infarction in the mouse. A schematic of the study design is provided. Panels A and B show representative images of TTC stains for infarct size measurement in vehicle- and 16673-34-0-treated mice. Panel C shows a significant increase of caspase-1 activity in the heart 24 hours following ischemia-reperfusion, and a significant (>90%) reduction with 16673-34-0. Panels D and E show a significant (>40%) reduction in infarct size with 16673-34-0, without differences in the area-at-risk. Panel F shows a significant increase in serum cardiac troponin I levels 24 hours after ischemia-reperfusion, and significantly lower levels (~70%) in mice treated with 16673-34-0.

Figure 8:
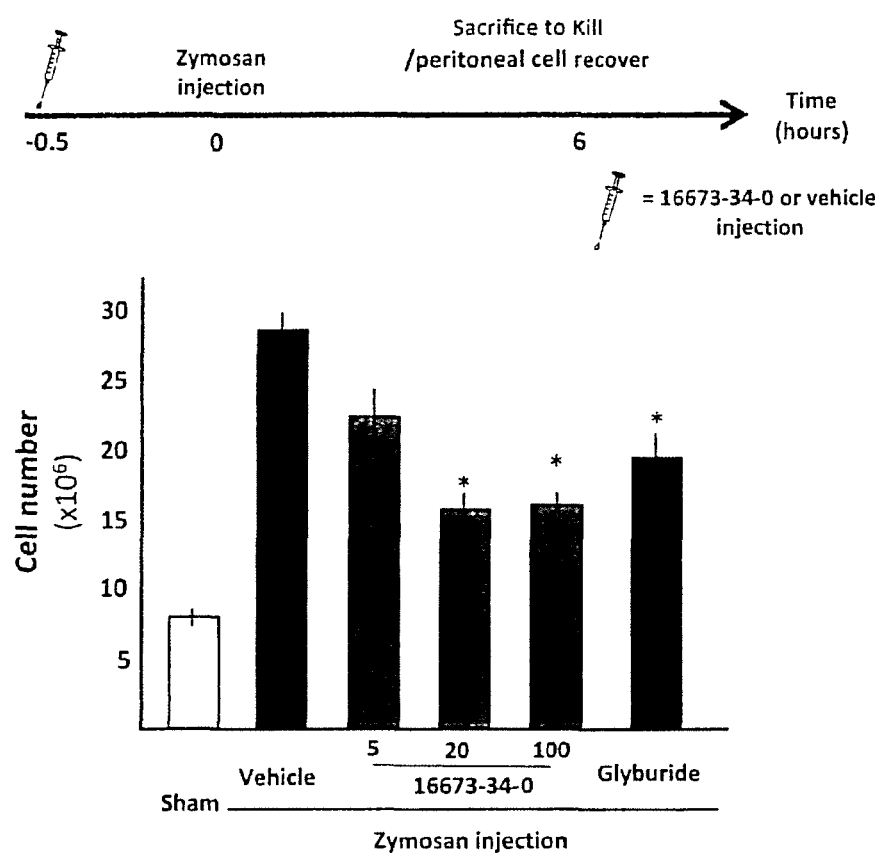

FIG. 8. 16673-34-0 inhibits the NLRP3 inflammasome in a model of acute peritonitis in the mouse. A schematic of the study design is provided. A significant increase in the number of cells recovered from the peritoneal lavage was seen 6 hours after treatment with zymosan, and it was significantly reduced by treatment with 16673-34-0 or glyburide.

FIGS. 9A and B. Treatment of acute reperfused myocardial infarction in vivo. A, caspase-1 activity and B, cTnI level after a single dose of 16673-34-0 or vehicle.

FIGS. 10A and B. Treatment of acute reperfused myocardial infarction in vivo. A, appearance of heart tissue and B, Left Ventricular Fractional Shorting (LVFS) at day 7 after a single dose of 16673-34-0 or vehicle.

FIG. 11A-D. Treatment of acute non-reperfused myocardial infarction in vivo. A, appearance of heart tissue, B, Left Ventricular End Diastolic Diameter (LVEDD), C, Left Ventricular End-Systolic Diameters (LVESD), and D, Left Ventricular Fractional Shorting (LVFS) at day 7 after daily treatment with 16673-34-0 or vehicle.

FIG. 12A-C. Treatment of acute non-ischemic myocardial injury in vivo. A, appearance of heart tissue, B, 5 fibrosis, and C, LVFS at day 10 after daily treatment with 16673-34-0 or vehicle.

Figure 13:
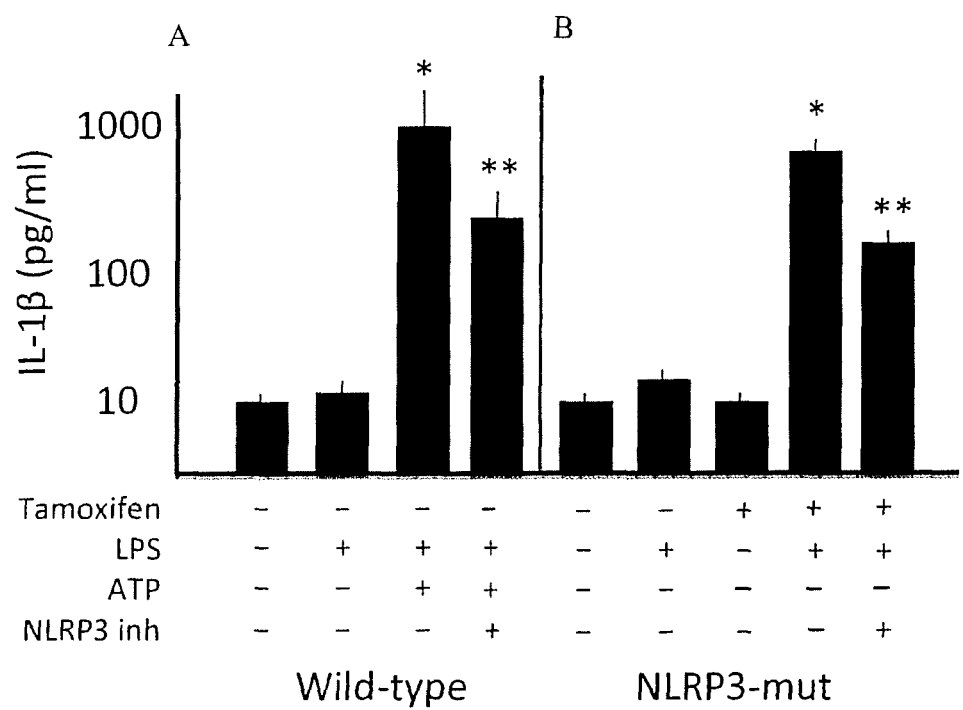

FIGS. 13 A and B. Production of IL-1β in bone-marrow derived mononuclear cells (BMDMC) in vitro in A, wild-type and B, NLRP3-mut mice. Data was obtained in wt mice following stimulation with LPS or LPS plus ATP, and in NLRP3-mut mice and treatment with LPS alone, in the presence and absence of an NLRP3 inhibitor.

Figure 14:
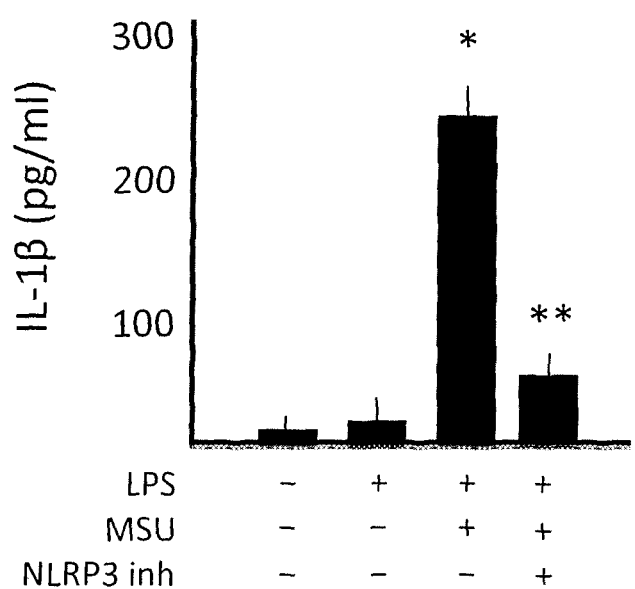

FIG. 14. Production of IL-1β in cultured macrophages (J774A.1) in vitro following stimulation with LPS and monosodium urate (MSU), and treatment with the NLRP3 inhibitor. Cultured macrophages produce large amounts of IL-1β after stimulation with LPS and MSU, which is significantly inhibited by the NLRP3 inhibitor.

FIGS. 15 A and B. A single dose of GA2 or GA3 given intraperitoneally at reperfusion inhibits the NLRP3 inflammasome and reduces infarct size in AMI in the mouse (wherein as glyburide does not). A, Structures of GA2, GA3 and glyburide (Gly); B, infarct size (% area at risk, AAR) after administration of vehicle, Gly, GA2 or GA3.

FIGS. 16A and B. A single dose of GA2 or GA3 given intraperitoneally at reperfusion inhibits the NLRP3 inflammasome and reduces infarct size in AMI in the mouse (wherein as glyburide does not). A, structures of GA2, GA3 and GA1; B, infarct size (% AAR) after administration of vehicle, GA1, GA2 or GA3.

Figure 17:
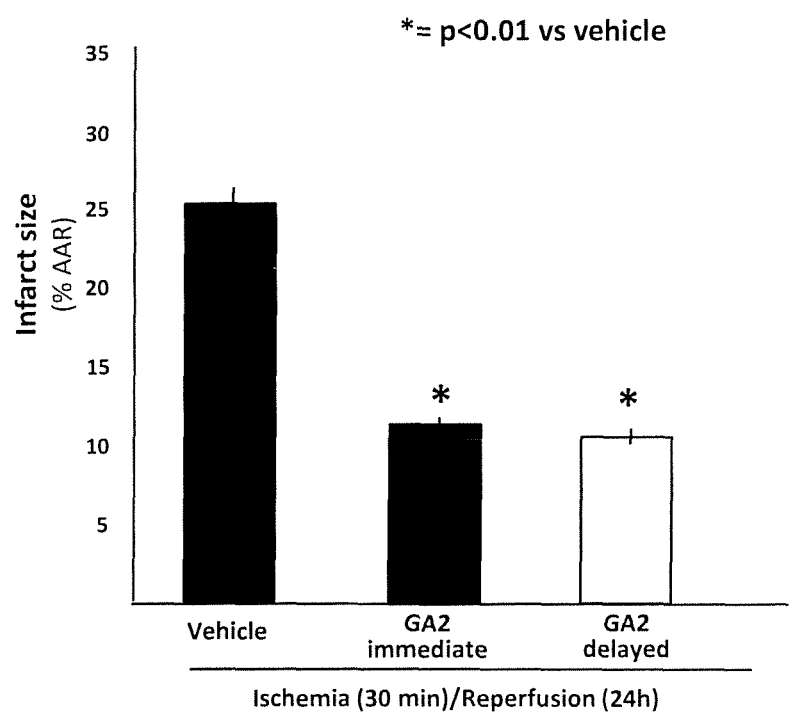

FIG. 17. A single dose of GA2 given i.p immediately at reperfusion or delayed until after 1 hour of reperfusion reduces infarct size in acute myocardial infarction in the mouse. Infarct size is shown.

DETAILED DESCRIPTION

Analogs that inhibit cryopyrin (NLRP3, NLP3) inflammasome formation and activity are provided, as are methods of their use to treat various NLRP3-inflammasome related diseases and conditions. The analogs have the generic structures of Formula I and Formula II:

Formula I

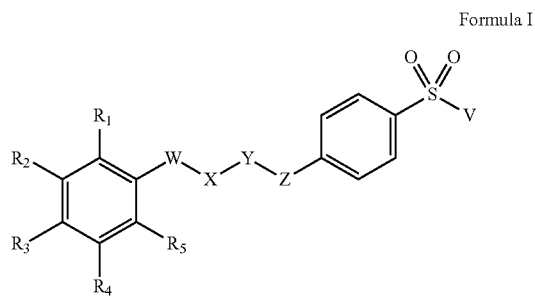

It is an object of this invention to provide a compound of Formula I:

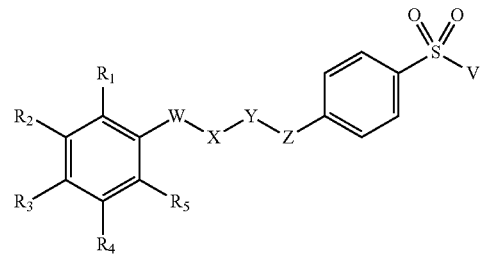

wherein $R_1$ is unbranched, branched, saturated, unsaturated, cyclic or acyclic, substituted or unsubstituted C1-C8 alkyl or is unbranched, branched, saturated, unsaturated, cyclic or acyclic, substituted or unsubstituted C1-C8 alkoxyl;

$R_4$ is halogen, amino, nitro or cyano;

$R_2$, $R_3$ and $R_5$ may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;

W is unbranched, branched, saturated, unsaturated, substituted or unsubstituted C1-C4 alkyl and may be present or absent;

X is carbonyl or $CH_2$ or $CH_2OH$; and

Y is NH, O, or S; and

Z is C1-C5 unbranched, branched, saturated, unsaturated, cyclic or acyclic, substituted or unsubstituted alkyl, or NHR wherein R is selected from C1-C5 unbranched, branched, saturated, unsaturated, cyclic or acyclic, substituted or unsubstituted alkyl V is i) $NR^1R^2$ where $R^1$ and $R^2$ are H or $C_1$-$C_6$ alkyl and may be the same or different; or ii) a saturated heterocycle comprising N bonded directly to S; or iii) an unsubstituted or substituted guanidine moiety.

In some aspects, the compound of Formula I is a compound of Formula II:

Formula II

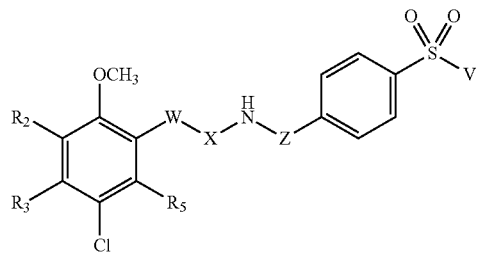

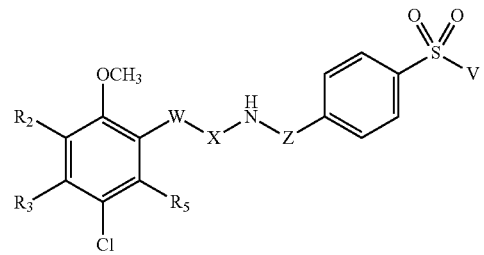

wherein

R2, R3 and R5 may be the same or different and are independently selected from H, C1-C8 unbranched, branched, saturated, unsaturated, cyclic or acyclic, substituted or unsubstituted alkyl, C1-C8 unbranched, branched, saturated, unsaturated, cyclic or acyclic, substituted or unsubstituted alkoxyl, C1-C8 unbranched, branched, saturated, unsaturated, cyclic or acyclic, substituted or unsubstituted alkylcarbonyl, halogen, hydroxyl, amino, nitro and cyano;

W is unbranched, branched, saturated, unsaturated, substituted or unsubstituted C1-C4 alkyl and may be present or absent;

X is carbonyl or $CH_2$ or $CH_2OH$; and

Z is C1-C5 unbranched, branched, saturated, unsaturated, cyclic or acyclic, substituted or unsubstituted alkyl, or NHR wherein R is selected from C1-C5 unbranched, branched, saturated, unsaturated, cyclic or acyclic, substituted or unsubstituted alkyl.

V is i) $NR^1R^2$ where $R^1$ and $R^2$ are H or $C_1$-$C_6$ alkyl and may be the same or different; or ii) a saturated heterocycle comprising N bonded directly to S; or iii) an unsubstituted or substituted guanidine moiety.

For the compounds disclosed herein:

Exemplary halogens include but are not limited to: F, Cl, Br and I.

"Cyclic" hydrocarbons (alkyls) include pentyl- and benzyl-moieties, which may be substituted or unsubstituted.

Exemplary alkyl groups include but are not limited to: $CH_3$—, $CH_3CH_2$—, $CH_3(CH_2)_2$—$CH_3(CH_2)_3$—, $CH_3(CH_2)_4$—, $CH_3(CH_2)_5$—, $CH_3(CH_2)_6$—, $CH_3(CH_2)_7$—, which may be substituted or unsubstituted, or propargyl.

Exemplary alkoxyl groups include but are not limited to: $CH_3O$—, $CH_3CH_2O$—, $CH_3(CH_2)_2O$—$CH_3(CH_2)_3O$—, $CH_3(CH_2)_4O$—, $CH_3(CH_2)_5O$—, $CH_3(CH_2)_6O$—, $CH_3(CH_2)_7O$—, which may be substituted or unsubstituted, or ethynyloxy.

"Substituted" refers to the inclusion of a heteroatom or heteroatoms such as S, N, O, NO, OH, etc. within or attached to an alkyl chain or cyclic hydrocarbon An exemplary compound is depicted in Formula III:

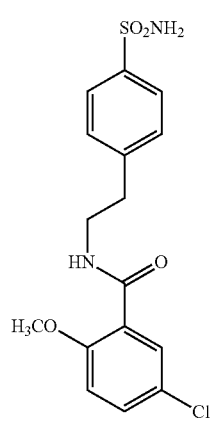

Formula III ("GA2")

moylphenyl)-ethyl]-benzamide) is also referred to as 16673-34-0. In addition, Formula III is represented by compound 5 of Scheme I in the Examples. Another exemplary compound is depicted in Formula IV:

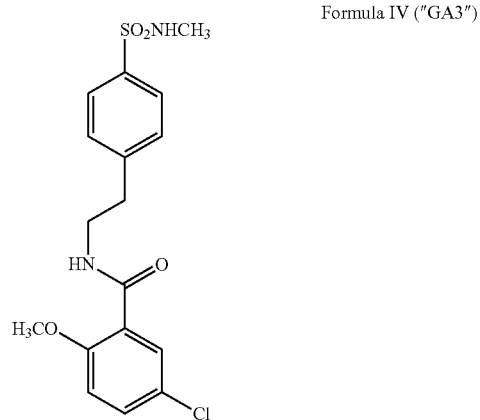

Formula IV ("GA3")

Another exemplary compound is depicted in Formula V:

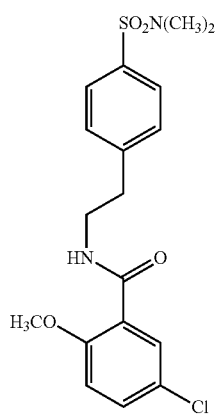

Formula V

Another exemplary compound is depicted in Formula VI:

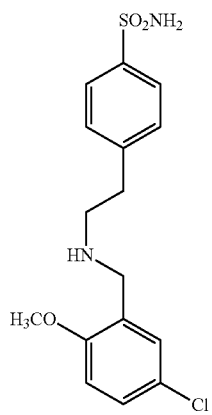

Formula VI

In the Examples section below and the accompanying figure legends, Formula III (5-chloro-2-methoxy-N-[2-(4-sulfa- Another exemplary compound is depicted in Formula VII:

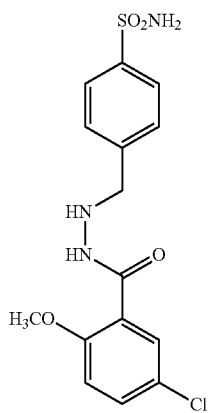

Formula VII

The analogs disclosed herein are used to treat any disorder or condition associated with (e.g. caused by or related to or which exacerbates) unwanted NLRP3 inflammasome formation and/or activation and/or consequences of such formation and/or activation, e.g. unwanted production of pro-inflammatory cytokines pro-IL-1β and pro-IL-18. Such diseases/conditions may be caused by so-called sterile inflammation (e.g. various inflammatory diseases, second wave inflammation after heart attack, stroke or other ischemic or traumatic injury), or by inflammation that is caused by an infection (e.g. by an infectious organism such as a bacterium or virus). Such diseases and conditions result from a wide array of stimuli. For example, numerous microbes including various bacteria, viruses, fungi, and protozoan parasites can activate the NLRP3 inflammasome, e.g., the bacterial toxin nigericin has also been reported to induce the activation of NLRP3 by causing potassium efflux in a pannexin-1-dependent manner. In addition to microbial activators, endogenous "danger" signals such as ATP, monosodium urate (MSU) and amyloid-β activate the NLRP3 inflammasome, as do various other types of cellular damage resulting e.g. from metabolic stress, ischemia and trauma. The NLRP3 inflammasome is implicated in metabolic disorders and sterile inflammatory responses including type II diabetes mellitus, gout, Alzheimer's disease and ischemia. A number of endogenous and exogenous crystalline molecules activate the NLRP3 inflammasome, e.g. uric acid crystals and calcium pyrophosphate dihydrate, the causative agents of gout and pseudogout respectively. Fibrillar amyloid-β, associated with the pathogenesis of Alzheimer's disease, also activates the NLRP3 inflammasome. Silica and asbestos particles, which cause the fibrotic lung disorders silicosis and asbestosis respectively, also activate the NLRP3 inflammasome. Release of ATP from necrotic cells is a danger signal that activates the innate or sterile inflammatory immune response. Inhibiting NLRP3 inflammasome activation has beneficial effects in preventing the damage mediated by the sterile inflammatory response in diseases such as renal-, cardiac-, and cerebral-ischemia. In addition, necrosis-induced sterile inflammation in trauma and secondary to infections and sepsis are modulated by the inhibitors of the NLRP3 pathway described herein. The NLRP3 inflammasome can also be activated by molecules associated with stress or danger, including crystalline and particulate substances.

Examples of particular auto-inflammatory diseases which may be prevented or treated by the agents described herein include but are not limited to:

i) Joint, bone and muscle diseases such as rheumatoid arthritis, psoriatic arthritis, osteoarthritis, ankylosing spondylitis, erosive osteoarthritis of the hand, recurrent multifocal osteomyelitis, traumatic knee injury; relapsing polychondritis, etc;

ii) Hereditary systemic autoinflammatory diseases such as familial Mediterranean fever (FMF), cryopyrin-associated periodic syndrome (CAPS); Muckle-Wells Syndrome, TNF receptor-associated periodic syndrome (TRAPS), hyper-IgD syndrome (HIDS), periodic fever, aphthous stomatitis, pharyngitis and adenitis (PFAPA), deficiency of interleukin-1 (IL-1) receptor antagonist (DIRA), etc;

iii) Systemic inflammatory diseases such as systemic juvenile idiopathic arthritis, adult-onset Still's disease, Schnitzler syndrome, Behcet's disease, PFAPA (Periodic Fever, Apthous Sstomatitis, Pharyngitis, Adenitis), SAPHO (synovitis, acne, pustulosis, hyperostosis, osteitis) syndrome, macrophage activation syndrome, etc; and iv) Common inflammatory diseases such as gout, Type 1 diabetes, Type 2 diabetes, metabolic syndrome, insulin resistance, stroke, heart attack, myocarditis, cardiac toxicity due to drug or radiation, ischemic heart disease, cardiomyopathy on a familial or genetic basis, heart failure, cardiac arrest and anoxic brain injury, acute and chronic lung injury due to infection, ischemia, toxin, trauma; dry eye syndrome, pustular psoriasis; neutrophilic dermatoses; acute or chronic hepatitis due a virus, toxin, ischemia or drug; acute or chronic renal injury due to ischemia, hypertension, diabetes, toxin or drugs; sepsis, septic shock; dementia including Alzeheimer's disease; etc.

In one aspect, the compounds are used to treat sterile inflammatory conditions such as those which occur in conjunction with AMI, e.g. the second wave of inflammation during adverse cardiac remodeling, etc. which leads to decreased cardiac function, heart failure, and premature death. Thus, adverse cardiac remodeling may be prevented or treated by administration of the compounds disclosed herein.

In another aspect, the compounds are used to treat peritonitis. "Peritonitis" refers to an inflammation of the peritoneum, the thin tissue that lines the inner wall of the abdomen and covers most of the abdominal organs. Peritonitis may be localized (e.g., due to appendicitis or diverticulitis but before perforation) or generalized (e.g. after perforation for example due to rupture of a hollow organ as may occur in abdominal trauma or appendicitis). Peritonitis may result from infection per se or from a non-infectious process.

The present invention provides compositions comprising the compounds described herein, and/or pharmaceutically acceptable salts of the compounds. The compositions are generally for use in preventing or treating inflammation, e.g. inflammation caused by formation and activity of NLRP3 inflammasomes. The compositions include one or more substantially purified compounds as described herein, and a pharmacologically suitable (compatible) carrier. The preparation of such compositions is known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the compositions may contain other agents with different but complementary activities, e.g. other anti-inflammatory agents, analgesics, blood thinners, antihistamines, etc. If it is desired to administer an oral form of the compositions, various thickeners, flavorings, diluents, emulsifiers, dispersing aids or binders and the like may be added. The compositions of the present invention may contain any such additional ingredients so as to provide the composition in a form suitable for administration. The final amount of compound in the formulations may vary. However, in general, the amount in the formulations will be from about 1-99%. Still other suitable formulations for use in the present invention can be found, for example in Remington's Pharmaceutical Sciences, Philadelphia, Pa., 19th ed. (1995).

As used herein, "pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Precursors (generally inactive precursors) of the compounds which are metabolized after administration to yield the compounds/active agents described herein in an active form are also encompassed.

The therapeutic agents described herein are used alone or in combination with other suitable agents, e.g. other agents that prevent or treat inflammation (for example, by another mechanism), including but not limited to: IL-1R antagonists such as anakinra; monoclonal antibodies against interleukin 1β such as canakinumab (Ilaris); various interleukin 1 binding proteins such as rilonacept; and the like. Accordingly, the compositions provided herein may include one or more of these additional agents.

The compositions (preparations) of the present disclosure may be administered by any of the many suitable means which are well known to those of skill in the art, including but not limited to: by injection (e.g. intravenous, intraperitoneal, intramuscular, subcutaneous, intra-aural, intraarticular, intramammary, and the like), by absorption through epithelial or mucocutaneous linings (e.g., nasal, oral, vaginal, rectal, gastrointestinal mucosal linings, and the like), by inhalation, orally, intranasally, by ingestion of a food or probiotic product containing the antimicrobial peptide, topically (e.g. on areas such as eyes, skin, in ears or on inflamed areas), as eye drops, via sprays, incorporated into dressings or bandages (e.g. lyophilized forms may be included directly in the dressing), etc. Generally, the mode of administration is by injection so as to effect systemic distribution of the agent, or locally by direct application, via an appropriate means, at or near a site of inflammation or a site where inflammation is likely to occur.

The amount of a compound that is administered varies depending on several factors, including the disease or condition being treated, the stage of the disease, the overall health of the subject, the subject's age, gender and weight, etc. In general, the amount is in the range of from about 0.01 to about 100 mg/kg of body weight, and usually is in the range of from about 1 to about 20 mg/kg of body weight. The subjects (patients) that are treated as described herein are generally mammals, e.g. humans, but veterinary applications of this technology are also encompassed, e.g. for companion pets such as cats and dogs.

The compounds of the disclosure are utilized to prevent and/or to treat conditions and/or diseases associated with (e.g. caused by) NRLP3 inflammasome formation and/or activity (i.e. to treat NRLP3 inflammasome-associated inflammation). By "prevent" we mean that the compounds are administered prophylactically to a subject who is likely to develop the disease or condition, but before symptoms or indications of disease develop, or early in development. For example, subjects who have experienced an AMI may be treated as described herein in order to prevent subsequent adverse cardiac remodeling during the "second wave" of inflammation. Alternatively, or in addition, the compounds may be administered in order to treat conditions/diseases that have already developed (e.g. when symptoms are already being exhibited, or are observable or measurable). In this case, administration of the compounds ameliorates and may reverse the symptoms, or at least arrest the disease (e.g. prevent further disease development or progress). Those of skill in the art will recognize that while a goal of prevention or treatment may be to completely prevent or alleviate disease symptoms, much benefit can also accrue if symptoms not fully eradicated but are lessened, decreased or their onset is slowed, even though a full-blown cure is not effected.

Methods of treating NRLP3 inflammasome-related diseases are provided. Such methods may include a step of identifying a subject in need of such treatment (e.g. a subject with one or more symptoms of an NRLP3 inflammasome-related disorder, or a subject who is likely to develop such a disorder). For example, patients who have had a heart attack (or other type of damage to the heart muscle) may be treated, as may patients who are exhibiting the first signs of myocardial infarction (or damage), or even patients for whom there is reason to suspect that an AMI (or other damage) is likely to occur, e.g. patients who are taking other drugs which are known to damage heart tissue, or patients with genetic disorders which predispose them to heart disease, etc. The same is true for other conditions that are treated by the agents disclosed herein, i.e. a subject suitable for undergoing treatment may have one or more readily observable symptoms, or early symptoms, or a predisposition to development of the disease (e.g. genetically, due to life style, due to exposure to a substance that is known to cause inflammation, etc.) that is being treated.

As indicated above, the present invention inter alia provides the specified compounds for use in a method of: method of preventing or treating NRLP3 inflammasome-associated inflammation, including sterile inflammations associated with post-AMI remodeling, etc, as well as acute inflammation, or acute inflammatory response, which may occur in variety of illness in which an injury induces inflammation. As an example of acute inflammation we show data on the acute inflammatory response in AMI and in acute peritonitis. For the avoidance of doubt, in this aspect the present invention may provide the specified compound for use as a medicament in the specified method. Further, the present invention may provide the specified compound as an active therapeutic ingredient in the specified method. Further, the present invention may provide the specified compound for use in a method of treatment of the human or animal body by therapy, the method comprising the specified method.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The synthesis of the exemplary compounds is described in Schemes 1-3.

Scheme 1:

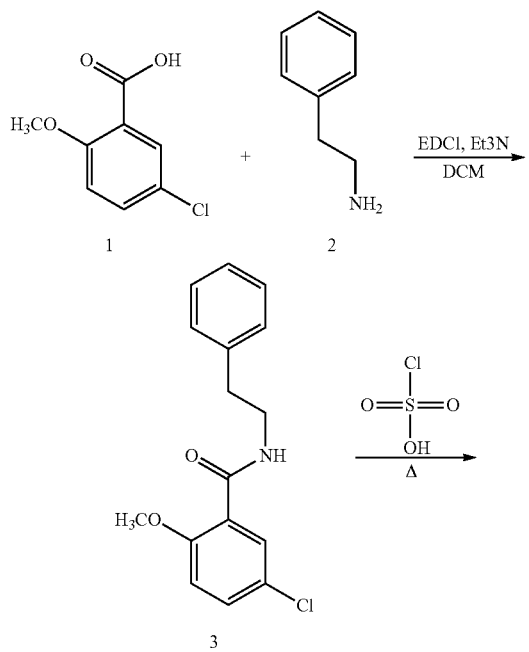

-continued
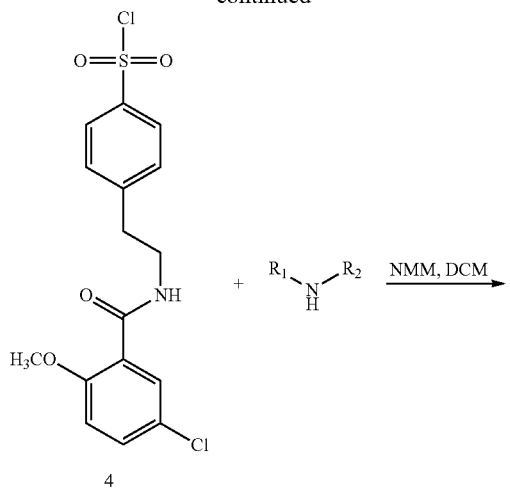
Scheme 2:
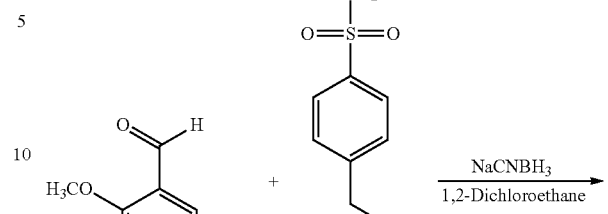
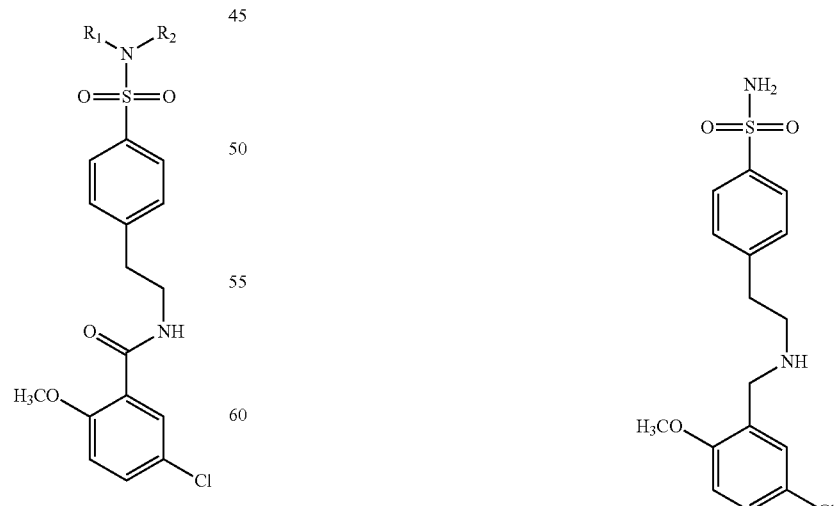
5 R1 = H, R2 = H
6 R1 = H, R2 = CH3
7 R1 = CH3, R2 = CH3

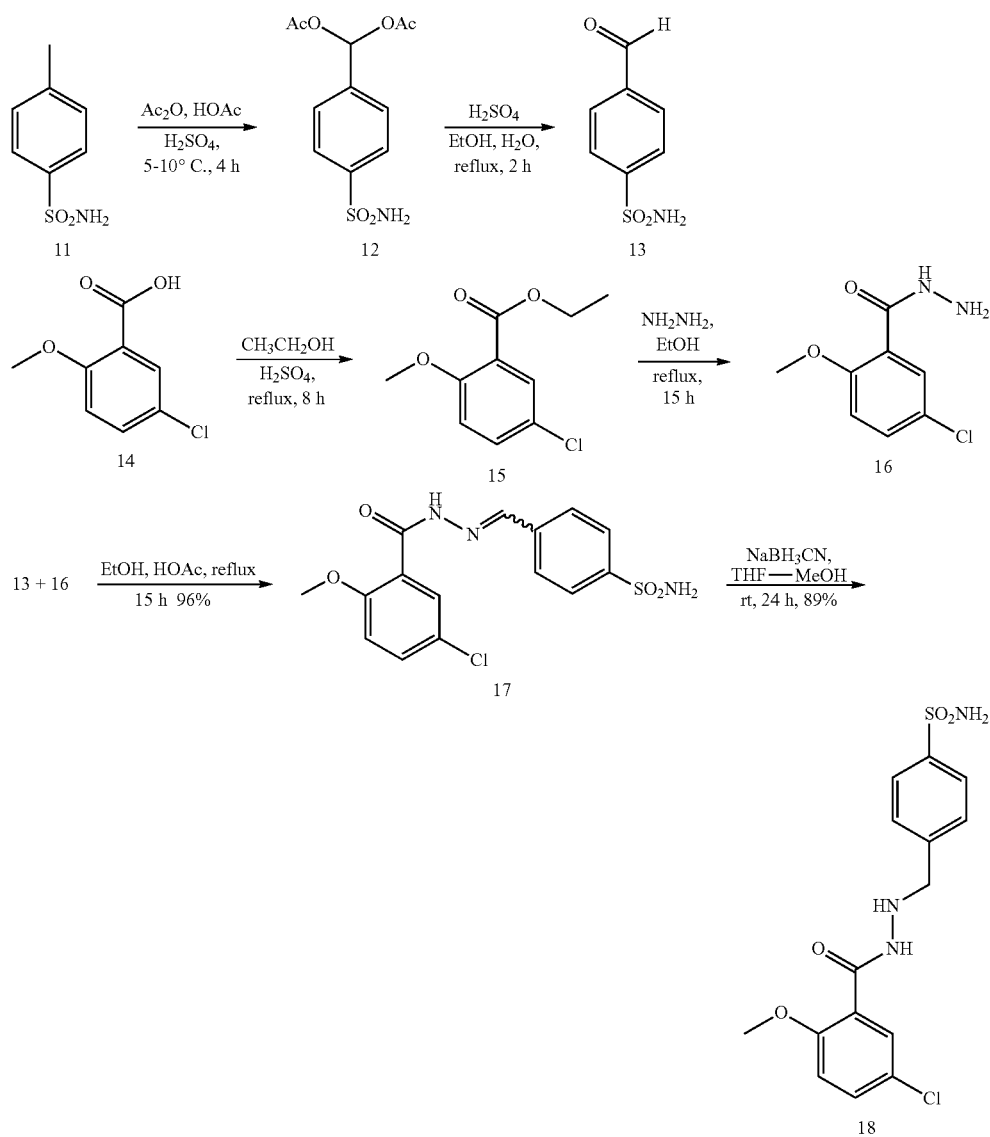

Scheme 3

Example 1. Preparation of 3

4-Chloro-2-methoxy-benzoic acid (5.35 mmol, 1 equiv.) was dissolved in anhydrous DCM (25 mL) and cooled to 0° C. To this EDC (8.025 mmol, 1.5 equiv.) and triethylamine (8.025 mmol, 1.5 equiv.) were added, and the reaction was stirred for 1 h. Phenethylamine (5.35 mmol, 1 equiv.) was then added, and the reaction was allowed to warm to room temperature and stirred overnight. The reaction was then washed twice with brine and concentrated. The amide product was purified by column chromatography with a gradient of 20% EtOAc/80% Hexane to 60% EtOAc/40% Hexane with an overall yield of ~40%. The chemical structure of 3 was confirmed with NMR and purity was confirmed with HPLC and LC-MS.

Example 2. Preparation of 4

Chlorosulfonic acid (2 mL) was cooled on an acetone and dry ice bath, and to this was added the amide starting material 3 (2.76 mmol) in a small amount of DCM (0.5 mL). The reaction was allowed to warm to room temperature, and then heated to 100° C. for 1 h. The reaction was cooled to room temperature and then slowly poured on crushed ice. The product was extracted from this ice/water layer into DCM, and concentrated. The chlorosulfonyl product 4 was purified by column chromatography with a gradient of 25% EtOAc/75% Hexane to 60% EtOAc/40% Hexane with an overall yield of ~40%. The chemical structure of 4 was confirmed with NMR and purity was confirmed with HPLC and LC-MS.

Example 3. Preparation of 5 (GA2, Formula III); 6 (GA3, Formula IV) and 7

The sulfonyl chloride 4 (1.00 mmol, 1 equiv.) was dissolved in anhydrous DCM (5 mL). To this aqueous $NH_4OH$, or the substituted amine (2.00 mmol, 2 equiv.) and N-methyl morpholine (0.5 mL) were added, and the reaction was stirred overnight. The sulfonamide product was purified by column chromatography with a gradient of 100% DCM to 95% DCM/5% MeOH with an overall yield of ~80%.

Compound 5: 1H NMR (400 MHz, DMSO-d) δ 8.25 (t, J=5.52 Hz, 1H), 7.77 (d, J=8.28 Hz, 2H), 7.65 (d, J=3.01 Hz, 1H), 7.50 (dd, J=2.89, 8.91 Hz, 1H), 7.45 (d, J=8.28 Hz, 2H), 7.28 (s, 2H), 7.15 (d, J=8.78 Hz, 1H), 3.81 (s, 3H), 3.54 (q, J=6.30 Hz, 2H), 2.92 (t, J=7.15 Hz, 2H).

Compound 6: 1H NMR (400 MHz, DMSO-d) δ 8.17 (d, J=2.76 Hz, 1H), 7.82 (d, J=8.28 Hz, 2H), 7.41 (d, J=8.53 Hz, 2H), 7.39 (dd, J=2.89, 8.91 Hz, 1H), 6.88 (d, J=8.78 Hz, 1H), 4.26 (q, J=5.19 Hz, 1H), 3.80 (s, 3H), 3.75 (q, J=6.78 Hz, 2H), 3.02 (t, J=6.78 Hz, 2H), 2.68 (d, J=5.52 Hz, 3H).

Compound 7: 1H NMR (400 MHz, DMSO-d) δ 8.16 (d, J=2.76 Hz, 1H), 7.74 (d, J=8.30 Hz, 2H), 7.42 (d, J=8.30 Hz, 0H), 7.38 (dd, J=2.76, 8.78 Hz, 1H), 6.88 (d, J=8.78 Hz, 1H), 4.12 (q, J=7.03 Hz, 1H), 3.80 (s, 3H), 3.76 (q, J=6.00 Hz, 1H), 3.02 (t, J=6.53 Hz, 2H), 2.71 (s, 6H).

Example 4. Detailed Preparation of the Compound of Formula IV, Also Referred to as "GA3" Herein In the synthetic scheme below, the compound of Formula IV is referred to as "5" in order to preserve naming conventions for chemical synthetic schemes; the compound is referred to elsewhere herein as "the compound of Formula IV" or "GA3" or "6" in Example 3.

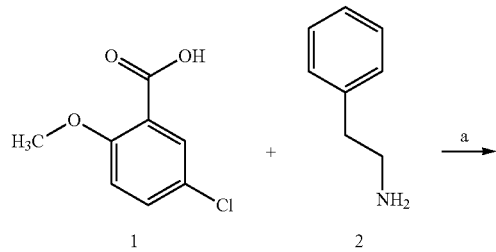

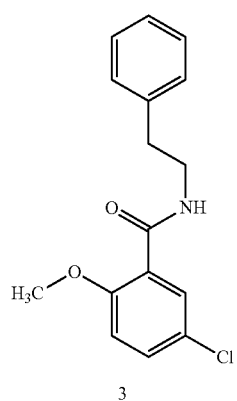

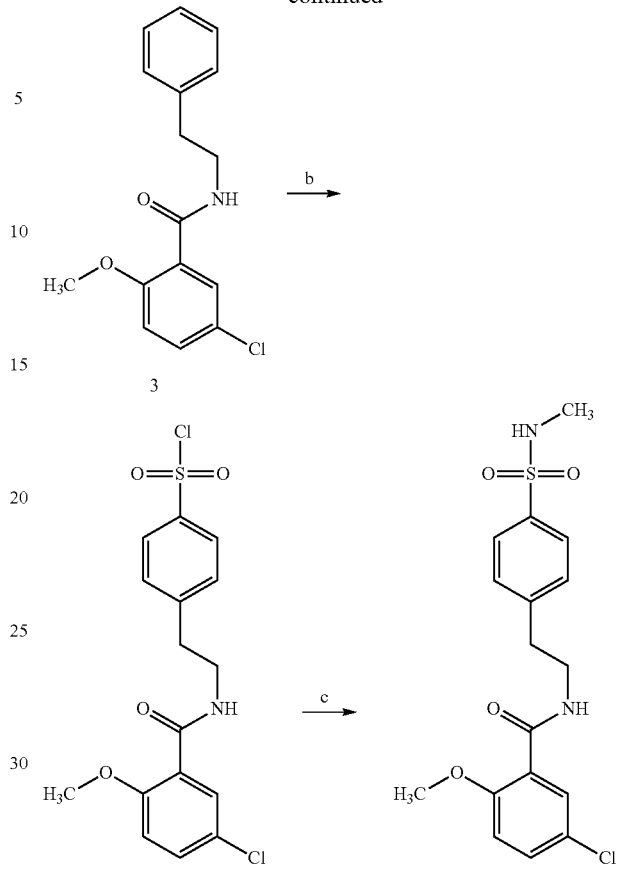

$^a$Reagents and conditions: a) EDC, HOBt, TEA, DCM; b) chlorosulfonic acid, 70° C.; c) methylamine HCl, NMM, MeOH, DCM. Abbreviations: DCM, dichloromethane; EDC, 1-ethyl-3-β-dimethylaminopropyl)carbodiimide; HOBt, 1-hydroxybenzotriazole hydrate; MeOH, methanol; NMM, N-methylmorpholine; TEA, triethylamine.

Experimental Procedure 5-chloro-2-methoxy-N-phenethylbenzamide (3). 5-Chloro-2-methoxybenzoic acid 1 (2.0 g, 10.7 mmol) was dissolved in DCM (100 mL) and cooled to 0° C. EDC (3.0 g, 16.0 mmol) was then added, and the solution was stirred for 30 min. HOBt (2.16 g, 16.0 mmol) was then added, and the solution was stirred for another 30 min. To this solution, 2-phenylethanamine 2 (1.3 g, 10.7 mmol) and TEA (2.98 mL, 21.4 mmol) were added, and the reaction was allowed to warm to room temperature and stirred overnight. The reaction was then washed with $H_2O$ (30 mL×3). The organic layer was concentrated and then purified by column chromatography (EtOAc/Hexanes: 20/80 to 50/50) to yield compound 3 (1.95 g, 63%) as a viscous oil. $^1$H NMR (400 MHz, CDCl$_3$) δ 8.19 (d, J=3.01 Hz, 1H), 7.82 (br. s., 1H), 7.36 (dd, J=3.00, 8.80 Hz, 1H), 7.34 (d, J=6.78 Hz, 2H), 7.27 (d, J=7.03 Hz, 2H), 7.26-7.28 (m, 1H), 6.85 (d, J=8.78 Hz, 1H), 3.77 (q, J=6.20 Hz, 2H), 3.74 (s, 3H), 2.93 (t, J=6.78 Hz, 2H); $^{13}$C NMR (100 MHz, DMSO-d6) δ 163.4, 155.7, 139.4, 131.5, 129.6, 128.7, 128.3, 126.1, 124.7, 124.3, 114.1, 56.2, 40.7, 34.9.

4-(2-[(5-chloro-2-methoxyphenyl)formamido]ethyl)benzene-1-sulfonyl chloride (4). Compound 3 (0.50 g, 1.73 mmol) was dissolved in DCM (2 mL). To this, excess chlorosulfonic acid (1 mL) was added, and the solution stirred at 70° C. for 2 h. The reaction was cooled to room temperature, and then poured over crushed ice. The product was extracted into DCM, and then concentrated under reduced pressure. The product was then purified by column chromatography (EtOAc/Hexanes: 20/80 to 50/50) to yield compound 4 (0.35 g, 52%) as a white solid. $^1$H NMR (400 MHz, CDCl$_3$) δ 8.17 (d, J=3.01 Hz, 1H), 8.00 (d, J=8.28 Hz, 2H), 7.81 (br. s., 1H), 7.50 (d, J=8.53 Hz, 2H), 7.39 (dd, J=2.76, 8.78 Hz, 1H), 6.89 (d, J=8.78 Hz, 1H), 3.81 (s, 3H), 3.77 (q, J=6.50 Hz, 2H), 3.08 (t, J=6.90 Hz, 2H); $^{13}$C NMR (100 MHz, DMSO-d6) δ 163.5, 155.7, 146.1, 139.8, 131.5, 129.5, 128.0, 125.6, 124.7, 124.3, 114.2, 56.2, 40.6, 34.6.

5-chloro-2-methoxy-N-(2-[4-(methylsulfamoyl)phenyl] ethyl)benzamide (5, GA3). Methylamine HCl (44 mg, 0.644 mmol) and N-methylmorpholine (0.1 mL) were added to MeOH (1 mL). Compound 4 (50 mg, 0.129 mmol) was dissolved in DCM (2 mL) and then added to the reaction, and the solution was stirred overnight at room temperature. The reaction was concentrated, and then dissolved in DCM and H$_2$O. The product was extracted into DCM, concentrated, and purified by column chromatography (DCM/MeOH: 100/0 to 95/5) to give compound 5 (42 mg, 85%) as a white solid. $^1$H NMR (400 MHz, CDCl$_3$) δ 8.17 (d, J=2.76 Hz, 1H), 7.82 (d, J=8.28 Hz, 2H), 7.41 (d, J=8.53 Hz, 2H), 7.39 (dd, J=2.89, 8.91 Hz, 1H), 6.88 (d, J=8.78 Hz, 1H), 4.26 (q, J=5.19 Hz, 1H), 3.80 (s, 3H), 3.75 (q, J=6.70 Hz, 2H), 3.02 (t, J=6.78 Hz, 2H), 2.68 (d, J=5.52 Hz, 3H); $^{13}$C NMR (100 MHz, DMSO-d6) δ 163.6, 155.7, 144.3, 137.2, 131.4, 129.5, 129.4, 126.7, 124.9, 124.3, 114.2, 56.2, 40.1, 34.6, 28.6.

Example 5. Preparation of 10

To a solution of 8 (2.93 mmol, 1 equiv.) and 9 (3.28 mmol, 1.12 equiv.) in 1,2-dichloroethane (100 mL) was added acetic acid (3.28 mmol, 1.12 equiv.). The mixture was stirred at room temperature for 1 h, then NaCNBH$_3$ (3.9 mmol, 1.3 equiv.) in methanol (30 mL) was added in a step-wise fashion. The mixture was stirred at room temperature overnight. Water (2 mL) was added to quench the reaction. Solvents were removed and the crude product of 10 was purified by column chromatography with DCM/MeOH (90/10). The chemical structure of 10 was confirmed with NMR and purity was confirmed with HPLC and LC-MS.

Example 6. Preparation of 13

Concentrated sulfuric acid (7 mL) was added dropwise to the mixture of acetic anhydride (80 mL) and acetic acid (40 mL). The mixture was cooled with ice bath. 4-Methylbenzenesulfonamide 11 (12 g, 70 mmol) was added and the reaction temperature was maintained beneath 5° C. Chromium oxide (8 g, 80 mmol) was added in batches. Then the reaction mixture was stirred for 4 h at 5-10° C., then the solution was poured into ice water (500 mL). The aqueous solution was extracted with DCM (3×100 mL). The combined organic phase was washed with brine, dried over anhydrous sodium sulphate and concentrated to give (4-sulfamoylphenyl)methylene diacetate 12 as a yellow oil.

The yellow oil which was achieved in the last step was dissolved in ethanol (10 mL). Water (10 mL) and concentrated sulfuric acid (2 mL) was added. The reaction mixture was heated to reflux and stirred for 2 h. Solvent was concentrated and the residue was diluted with water (50 mL). The aqueous solution was extracted with ethyl acetate (2×20 mL). The combined organic phase was dried over sodium sulphate and concentrated. The residue was purified by column on silica gel (eluent: Hexane/EA 3:1 to 1:1) to afford 13 as a white solid (1.5 g, 12% yield). $^1$H NMR (400 MHz, DMSO) δ 10.09 (s, 1H), 8.10 (d, J=8.3 Hz, 2H), 8.03 (d, J=8.3 Hz, 2H), 7.59 (s, 2H).

Example 7. Preparation of 16

To the solution of 5-chloro-2-methoxybenzoic acid 14 (500 mg, 2.68 mmol) in ethanol (15 mL) was added concentrated sulfuric acid (0.1 mL). The mixture was heated at reflux for 8 h. Solvent was concentrated in vacuum. The residue was diluted with ethyl acetate and the solution was washed with saturated NaHCO$_3$ solution and brine. The organic phase was dried over sodium sulphate and concentrated to give ethyl 5-chloro-2-methoxybenzoate 15 as colorless oil.

The colorless oil was diluted with ethanol (10 mL). Anhydrous hydrazine (258 mg, 8.04 mmol) was added. The reaction mixture was heated at reflux overnight, then allowed to cooled down to room temperature. White needle crystals were formed and were collected by filtration. The crystals were washed with ethanol and dried to afford the desired product 16 (330 mg, 61% yield). $^1$H NMR (400 MHz, DMSO) δ 9.30 (s, 1H), 7.61 (d, J=2.8 Hz, 1H), 7.49 (dd, J=8.9, 2.8 Hz, 1H), 7.15 (d, J=8.9 Hz, 1H), 4.54 (s, 2H), 3.86 (s, 3H).

Example 8. Preparation of 17

To the suspension of 13 (200 mg, 1 mmol) and 16 (217 mg, 1 mmol) in ethanol (5 mL) was added one drop of acetic acid. The mixture was heated at reflux overnight. The precipitate was collected by filtration and washed with ethanol (2×5 mL). The white solid was dried to give the desired product 17 (353 mg, 96% yield). $^1$H NMR (400 MHz, DMSO) δ 11.72 (s, 1H), 8.38 (s, 1H), 7.92-7.86 (m, 4H), 7.60 (d, J=3.1 Hz, 1H), 7.56 (dd, J=8.9, 2.8 Hz, 1H), 7.43 (s, 2H), 7.21 (d, J=8.9 Hz, 1H), 3.87 (s, 3H).

Example 9. Preparation of 18

The suspension of 17 (200 mg, 0.54 mmol) and NaBH$_3$CN (51 mg, 0.82 mmol) in THF-MeOH (v/v 1:1, 6 mL) was stirred for 24 h at room temperature. The reaction was quenched with concentrated hydrogen chloride (1 mL). Then the mixture was basified with saturated NaHCO$_3$ solution. White precipitate was formed and collected by filtration. The white solid was washed with water and dried to afford desired product 18 (178 mg, 89% yield). $^1$H NMR (400 MHz, Acetone) δ 9.26 (d, J=5.6 Hz, 1H), 7.95 (d, J=2.8 Hz, 1H), 7.89 (d, J=8.4 Hz, 2H), 7.62 (d, J=8.4 Hz, 2H), 7.49 (dd, J=8.9, 2.8 Hz, 1H), 7.18 (d, J=8.9 Hz, 1H), 6.56 (s, 2H), 5.54 (d, J=6.0 Hz, 1H), 4.17 (d, J=4.5 Hz, 2H), 3.92 (s, 3H).

Example 10. Inhibition of the NLRP3 Inflammasome Limits Myocardial Injury Following Ischemia-Reperfusion Introduction An intense inflammatory response occurs during acute myocardial infarction (AMI), and the intensity of such response predicts adverse outcome. The release of intracellular content during ischemic necrosis leads to the formation of a macromolecular structure, the inflammasome, in leukocytes and resident cells, including cardiomyocytes (FIG.

1). The activation of the inflammasome during injury greatly amplifies the inflammatory response by promoting the release of Interleukin-1β (IL-1β) and cell death. NLRP3 (NALP3 or cryopyrin) is one of the intracellular sensors, part of the Nod-like receptor (NLR) family, that trigger the formation of the inflammasome and activation of caspase-1. During cell death, extracellular ATP leads to an efflux of K+ from cell and subsequent NLRP3 activation. Silencing or genetic deletion of NLRP3 in the mouse limited the infarct size in experimental AMI, suggesting NLRP3 inflammasome as a viable target for pharmacologic inhibition.

The central role of NLRP3 in inflammatory diseases is highlighted in the cryopyrin-associated-period syndromes (CAPS), conditions in which constitutively active NLRP3 due to point-mutations leads to uncontrolled activation of the inflammasome leading to severe, often fatal, inflammatory disease. Clinically available NLRP3 inhibitors are, however, lacking. Glyburide, a widely used anti-diabetic drug (sulfonylurea) has NLRP3-inhibitory activity in vitro, but the use of glyburide as an inhibitor in vivo would require very high doses, e.g. several hundred-fold higher, than those used in diabetes, which would be inevitably associated with lethal hypoglycemia.

The cyclohexylurea moiety in the glyburide molecule is involved in the release of insulin by the pancreatic cells through inhibition of the KATP channels, yet it is not necessary for the NLRP3 inhibitory effect. This Example describes the inhibitory effects of 16673-34-0, an intermediate substrate in the synthesis of glyburide which is free of the cyclohexylurea moiety involved in insulin release, on the NLRP3 inflammasome activity. 16673-34-0 is also referred to as Formula III herein, and is compound 5 of Scheme I above.

Methods

Figure 2:
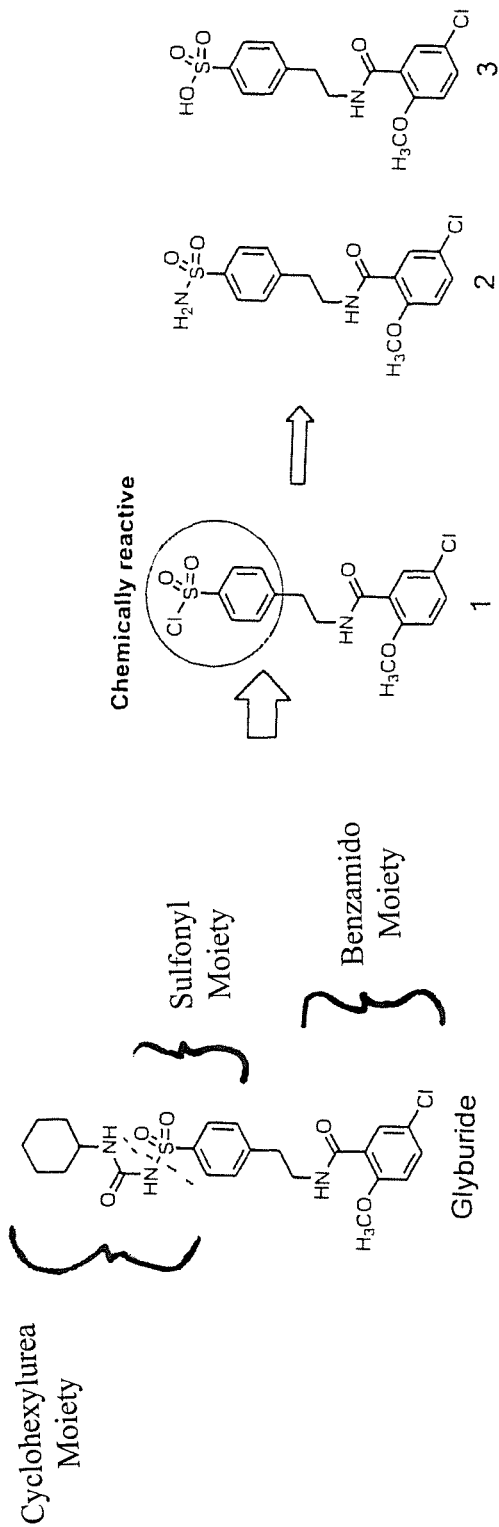
FIG. 2. Modification of Compound 1.

Design and synthesis of glyburide analogs. A recently reported analog containing a sulfonylchloride group (compound 1, FIG. 2) has been shown to retain some of the anti-inflammatory activity of glyburide but with no effect on insulin (Lamkanfi et al. J Cell Biol 2009; 18761-18770). However, compound 1 contains a sulfonyl chloride moiety which is chemically reactive, possibly rendering it nonselective as a cryopyrin inflammasome inhibitor. Therefore, chemically stable analogs 2 and 3 were designed to evaluate whether the sulfonamide and sulfonic acid moieties retained cryopyrin inflammasome inhibitory activity.

Figure 3:
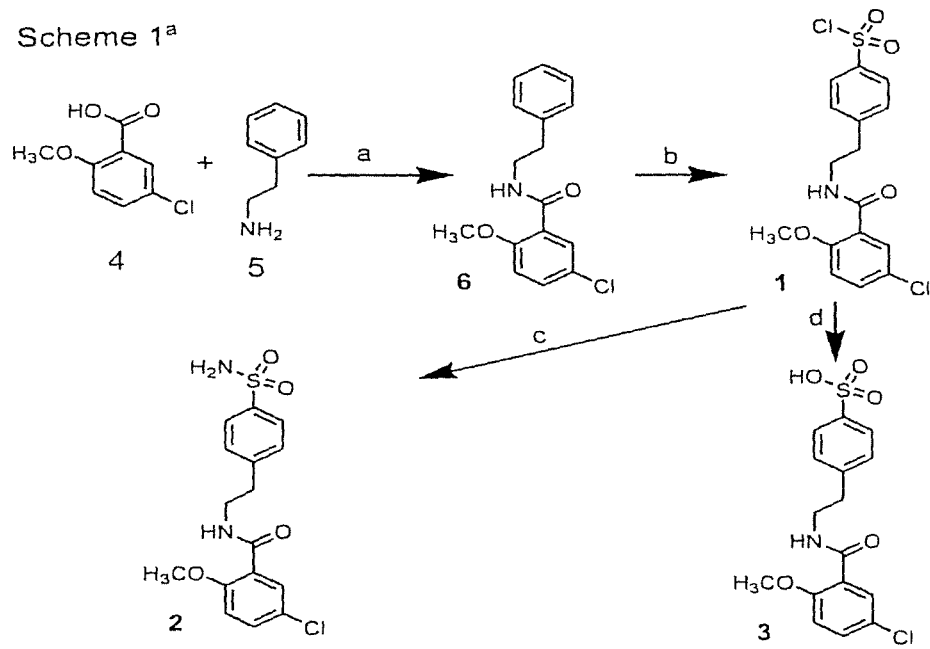
FIG. 3. Synthetic pathway of 5-chloro-2-methoxy-N-[2-(4-sulfamoylphenyl)-ethyl]-benzamide.

The synthesis of compounds 2 and 3 was achieved as shown in Scheme 1 (FIG. 3). Briefly, a coupling reaction of 4 (5-chloro-2-methoxybenzoic acid) and 5 (2-phenylethanamine), which are commercially available, in the presence of 1-theyl-3-β-dimethylaminopropyl)-carbodiimide (EDCI) affords 6 (the amide intermediate, 5-chloro-2-methoxy-N-(2-phenylethyl)-benzamide). Sulfonation of 6 to form 1 was achieved by adding chlorosulfonic acid to 5, followed by heating at 85° C. The sulfonamide analog 2 (5-chloro-2-methoxy-N-[2-(4-sulfamoylphenyl)-ethyl]-benzamide (16673-34-0)) was produced by reacting 1 with NH$_4$OH. Hydrolysis of 1 under refluxing conditions in H$_2$O yielded sulfonic acid 3 in good yield.

Determination of the Formation of Inflammasome In Vitro

J774A.1 cells, a murine macrophage cell line, were plated at 5×10$^4$ cells/well in a 96 multiwell plate for 24 hours in Roswell Park Memorial Institute (RPMI) medium (GIBCO®, Grand Island, N.Y.) supplemented with 10% of fetal bovine serum (FBS) (Sigma-Aldrich, St. Louis, Mo.). The cells were primed with Escherichia coli 0111:B4 lipopolysaccharide (LPS) (25 ng/mL; Sigma-Aldrich) (1 μg/ml) for 4 hours and then ATP (5 mM) for 30 minutes to induce NLRP3 inflammasome formation. The supernatants were collected and levels of IL-β were measured with a mouse IL-1β ELISA kit (Thermo Fisher Scientific, Princeton, N.J.). To test the inhibitory effects of 16673-34-0 on NLRP3 inflammasome activation, cells were co-treated with 16673-34-0 (400 μM) or Glyburide (400 μM) at the time of ATP for 30 minutes, and IL-1β levels were used as read-out.

In separate experiments, immortalized adult murine cardiomyocytes (HL-1) cells were used. Cells were cultured in Claycomb medium (Sigma-Aldrich) as suggested (Claycomb et al, Proc Natl Acad Sci USA 1998; 95:2979-2984) and then primed with LPS (25 ng/mL) for 2 h and treated with ATP (5 mM) for 1 hour, as previously described, to induce NLRP3 inflammasome formation (Mezzaroma et al, Proc Natl Acad Sci USA 2011; 108:19725-19730). HL-1 cells were then treated with 16673-34-0 (400 μM) or glyburide (400 μM) during the LPS priming phase, and then treated with ATP. Formation of the NLRP3 inflammasome in HL-1 cells was determined and quantified by ASC aggregation (immunohistochemistry), caspase-1 activity (enzymatic activity) and cell death (trypan blue exclusion method), as previously described. Briefly, for immunohistochemistry, HL-1 cells were plated on 24×24 mm glass covers slip coated with gelatin/fibronectin (0.02-0.5%) at 2.5×10$^5$ in 35-mm dishes 24 h before the experiment. ASC expression was detected as circumscribed cytoplasmic perinuclear aggregates and expressed as ASC-positive cell over the total cells per field, and ASC aggregates were quantified blindly by two different investigators. As readout for the NLRP3 inflammasome activation, caspase-1 enzymatic activity and cell death were evaluated. Briefly, HL-1 cells (2×10$^6$ cells) were plated in 90-mm dishes and NLRP3 inflammasome formation was induced as described above. After treatments, to measure caspase-1 activity, the cells were washed, harvested, and frozen. The pellet was resuspended using RIPA buffer (Sigma-Aldrich) containing a mixture of protease inhibitors (Sigma-Aldrich) and centrifuged at 16,200×g for 20 min. The supernatants were collected and the protein contents were quantified using the Bradford assay. The caspase-1 activity was determined by measuring the fluorescence produced by the cleavage of a fluorogenic substrate. The fluorescence was reported as arbitrary fluorescence units produced by 1 μg of sample per min (fluorescence/μg/min). Cell death in HL-1 cardiomyocytes was determined with a Trypan blue exclusion assay. Briefly, HL-1 cells were treated as described above, harvested and resuspended in 1 ml of Claycomb medium and incubated with 100 μL of 0.4% Trypan blue stain and incubated at room temperature for 5 min. Trypan blue positive cells were deemed nonviable and the percentage of cell death was measured as the ratio of trypan blue positive cells over total cell number per field. We used also nigericin (Enzo Life Sciences Inc, Farmingdale, N.Y.) 20 μM, a pore forming toxin allowing for K+ efflux from the cell in a way similar to that seen with ATP binding to the P2X7 receptor. To determine the specificity for the NLRP3 inflammasome and exclude effects other inflammasomes, HL-1 cells (1×10$^6$) were plated in 35 mm dishes and treated with flagellin or poly-deoxyadenylic-deoxythymidylic acid sodium salt (Poly(dA:dT)) to induce the NLRC4 and the AIM2 inflammasomes respectively, which do not involve the activation of the NLRP3 sensor. Flagellin (Enzo Life Sciences, Farmingdale, N.Y.), isolated from Salmonella typhimurium strain 14028, 0.7 ug/ml was added to the Claycomb medium in absence of fetal bovine serum (FBS). In order to induce the NLRC4 inflammasome, cells were first treated with flagellin using the Polyplus transfection kit (PULSin®, New York, N.Y.) for 4 hours and then treated with LPS (25 ng/ml) for 1 h. Poly(dA:dT) is a repetitive double-stranded DNA molecule used to induce AIM2 inflammasome formation. HL-1 cells were cultured in DMEM (Dulbecco's Modified Eagle Medium, Invitrogen) without FBS. Cells were incubated with Poly(dA:dT) (4 ug/ml) (InvivoGen, San Diego, Calif.) for 6 h and then treated with LPS (25 ng/ml) for 1 h. To evaluate the inhibitory effects of 16673-34-0 on the formation of the NLRC4 and AIM2 inflammasomes, HL-1 cells were treated with 16673-34-0 (400 µM) along with flagellin or Poly(dA:dT). Formation of the AIM2 and NLRC4 inflammasomes was determined and quantified by caspase-1 activity and cell death, as described above.

Administration of 16673-34-0 in the Mouse In Vivo

All the animal experiments were conducted under the guidelines of the "Guide for the care and use of laboratory animals" published by National Institutes of Health (revised 2011). The study protocol was approved by the Virginia Commonwealth University Institutional Animal Care and Use Committee. The 16673-34-0 was dissolved in dimethylsulfoxide (DMSO) (0.05-0.1 ml) and glyburide was used a control. In order to determine whether treatment with 16673-34-0 had any toxic effects in vivo, we measured weight, appetite and behavior after single and repeated intraperitoneal administrations in healthy control mice. Adult male (12-16 weeks old) out-bred Institute of Cancer Research (CDI) mice were supplied by Harlan Laboratories (Charles River, Mass.). We also measured capillary glucose levels (through prick stick of the tail and a point-of-care-testing glucometer) after single and repeated injections, over a range of concentration of 20-500 mg/Kg (N=4-6 per group).

Experimental Model of Acute Myocardial Infarction

Experimental acute myocardial infarction (AMI) was induced by transient myocardial ischemia for 30 min followed by reperfusion as described (Toldo et al. J Mol Cell Cerdiol 2011; 51:244-251). Briefly, mice were orotracheally intubated under anesthesia (pentobarbital 50 to 70 mg/kg), placed in the right lateral decubitus position, then subjected to left thoracotomy, pericardiectomy, and ligation of the proximal left coronary artery. The ligated coronary artery was released after 30 min before closure of the thorax. Sham operations were performed wherein animals underwent the same surgical procedure without coronary artery ligation (N=6-12 per group). To evaluate the effect of 16673-34-0, groups of mice were treated with 16673-34-0 (100 mg/kg in 0.05 ml) or DMSO solution (0.05 ml, vehicle) or NaCl 0.9% solution (0.05 ml, control) given 30 minutes prior to surgery, then repeated at time of reperfusion and then every 6 hours for 3 additional doses, the mice were then sacrificed at 24 hours, the heart removed and processed for the assessment of caspase-1 in the tissue or infarct size measurement. Caspase-1 activity was measured on protein extracted from frozen hearts homogenized in RIPA buffer. The Caspase-1 activity was measured and reported as described above.

Infarct size was measured using triphenyl tetrazolium chloride (TTC) (Sigma Aldrich) staining of viable myocardium 8 and the serum troponin I levels 24 hours after surgery were determined as markers of myocardial damage. Briefly, mice were anesthetized and the blood was drawn from the inferior vena cava and collected for the serum isolation. Mouse troponin I levels were determined by ELISA (Life Diagnostic Inc., West Chester, Pa.). In order to perform the infarct size staining, the heart was quickly removed after sacrifice and mounted on a Langendorff apparatus. The coronary arteries were perfused with 0.9% NaCl containing 2.5 mM $CaCl_2$. After the blood was washed out, the ligated coronary artery was closed again, and approximately 1 ml of 1% Evans blue dye (Sigma Aldrich) was injected as a bolus into the aorta until the heart 'not-at-risk' turned blue. The heart was then removed, frozen, and cut into 6 transverse slices from apex to base of equal thickness (approximately 1 mm). The slices were then incubated in a 10% TTC isotonic phosphate buffer (pH 7.4) at room temperature for 30 min. The infarcted tissue (appearing white), the risk zone (red), and the non-risk zone (blue) were measured by computer morphometry.

Experimental Model of Acute Peritonitis in the Mouse

Zymosan A triggers a NLRP3-inflammasome dependent inflammatory reaction when injected in the peritoneum. To determine the effects of 16673-34-0 on the NLRP3 inflammasome in vivo, independent of other potential effects on heart viability or function, we injected mice with 1 mg (0.1 ml) of zymosan A (Sigma-Aldrich) freshly prepared in sterile saline solution (0.9% NaCl) in the peritoneum, and after 6 hours mice were sacrificed by anesthesia overdose. The peritoneal cavity was immediately washed with 7 ml of cold PBS to recover peritoneal cells. Treatment with 16673-34-0 or an equal volume of DMSO (vehicle) was administered 30 min before the stimulation with zymosan A at different doses (5, 20 and 100 mg/kg in 0.1 ml) to determine the inhibitory effects on leukocyte recruitment in the cavity (N=4-12 per group). In addition to 16673-34-0, glyburide (132.5 mg/kg, equimolar to 100 mg/kg of 16673-34-0) was used as a positive control. The total number of leukocytes in the peritoneal cavity was measured by cell counting.

Statistical Analysis of Data

Continuous variables expressed as mean and standard error, and one-way ANOVA to compare between 3 or more groups followed by Bonferroni-corrected T tests for unpaired data was used. Survival analysis was performed using Kaplan Meyer curves and the LogRank (Mantel-Cox) analysis. $P<0.05$ was considered statistically significant.

Results 16673-34-0 Prevents the Formation of the NLRP3 Inflammasome In Vitro

Cultured mouse macrophages were treated with LPS followed by ATP to induce the formation of the NLRP3 inflammasome and measure the release of mature IL-1β in the supernatant (FIG. 4). Treatment with 16673-34-0 significantly limited IL-1β release after LPS and ATP challenge (FIG. 4). To determine whether 16673-34-0 inhibited the formation of the inflammasome also in cardiomyocytes, cultured adult HL-1 cardiomyocytes were treated with LPS and ATP which induced the formation of the NLRP3 inflammasome measured as macromolecular aggregates at immunocytochemistry for ASC, caspase-1 activity and inflammatory cell death, and all these effects were prevented by treatment with 16673-34-0 (Compound 2 in FIGS. 2 and 3). An intermediate of 16673-34-0 lacking the sulfonyl residue (Compound 6 in FIG. 3) also failed to inhibit caspase-1 and rescue the cells from inflammatory cell death in vitro (FIGS. 5A and B). ATP binding to the P2X7 receptor leads to K+ efflux to cell, accordingly the addition of nigericin, a pore forming toxin allowing for K+ efflux, to LPS led to the formation and activation of the NLRP3 inflammasome, also prevented by 16673-34-0 (FIG. 4). The activation of inflammasomes that use sensors other than NLRP3 (AIM2—triggered by exogenous dual strand DNA—or NLRC4—triggered by flagellin) were not inhibited by 16673-34-0 (FIG. 2), showing a selective effect on the NLRP3 inflammasome.

16673-34-0 has No Effects on Glucose Control in the Mouse In Vivo

At difference with glyburide, 16673-34-0 lacks the cycloxyurea moiety involved in the activation of the release of insulin, as such 16673-34-0 was well tolerated when given as high as 500 mg/kg for 7 days showing no significant effects on survival, body weight, appetite or behavior, and had no effects on plasma glucose levels, whereas glyburide led to a significant reduction in glucose levels as early as 2 hours and it was lethal within 3 days in 50% of mice treated with 100 mg/kg every 6 hours for 3 doses, and in 100% in 3 days after daily doses of 500 mg/kg, due to severe hypoglycemia in all cases (FIGS. 6A and B). These data show that 16673-34-0 has no measurable effect on glucose control in the mouse, as expected due to the structural lack of the cycloxyurea moiety.

16673-34-0 Inhibits the NLRP3 Inflammasome in Acute Myocardial Infarction in the Mouse.

To determine whether 16673-34-0 inhibited the NLRP3 inflammasome in vivo, we used a model of severe regional myocardial ischemia due to surgical coronary ligation (30 minutes) followed by reperfusion (24 hours). Treatment with 16673-34-0 led to a significant >90% reduction in caspase-1 activity (reflective of the formation of an active inflammasome) in the heart tissue measured 24 hours after ischemia (FIG. 7). Treatment with 16673-34-0 also led to a significant reduction in the infarct size measured with TTC (>40% reduction) or troponin I levels (>70% reduction) when compared with vehicle alone (FIG. 7). These data show that 16673-34-0 possesses powerful cardioprotective properties mediated by inhibition of the inflammasome. Treatment with an equivalent dose of glyburide led to a 100% mortality in mice with AMI (not shown).

16673-34-0 Inhibits the NLRP3 Inflammasome in a Model of Acute Peritonitis in the Mouse.

To determine whether 16673-34-0 inhibited the NLRP3 inflammasome in vivo in a model in which activation of the inflammasome is independent of the effects of myocardial ischemia/infarction, we used Zymosan A and induced a peritonitis which is known to be dependent upon intact NLRP3 inflammasome signaling and release of active IL-1β. Pre-treatment with 16673-34-0 (5, 20 and 100 mg/kg) limited the severity of the peritonitis measured as the intensity of the leukocyte infiltration in the peritoneal cavity, in a dose-dependent manner (FIG. 8). These data show that 16673-34-0 inhibits the formation and activation of the NLRP3 inflammasome in vivo, and suggests that the effects seen in the AMI model are likely due to a direct inhibition of the NLRP3 inflammasome and not exclusively to a reduction on the infarct size.

Thus, the glyburide analog, 16673-34-0, is a novel inhibitor of the NLRP3 inflammasome. While glyburide possesses NLRP3 inflammasome inhibiting properties in vitro, the dose required for this effect in vivo leads to severe and lethal hypoglycemia thus limiting its clinical use. When compared with glyburide, 16673-34-0 lacks the cycloxyurea moiety and therefore is not a sulfonylurea and it is not active on the KATP channels that regulate insulin release from pancreatic β-cells. 16673-34-0 inhibits the NLRP3 inflammasome in vitro and limits NLRP3 inflammasome mediated injury in an in vivo model of acute myocardial infarction and acute peritonitis. This is, to the best of our knowledge, the first pharmacologic inhibitor of the NLRP3 inflammasome to be tested in vivo. The finding of a protective effect of this pharmacologic NLRP3 inflammasome inhibitor confirms the central role of inflammation in AMI.

16673-34-0 has inhibitory effects on the NLRP3 inflammasome but not on NLRC4 or AIM2 inflammasomes. 16673-34-0 inhibits the aggregation of the NLRP3 inflammasome following LPS and $K^+$ efflux (but not after other NLPR3-independent stimuli) suggesting that it impedes the polymerization of the structure by interfering either with the activation of NLRP3 or aggregation with the scaffold ASC. Multiple diverse stimuli activate NLRP3 yet the effects of 16673-34-0 are maintained independent of which stimulus occurs, suggesting that 16673-34-0 interferes with downstream events involved in either NLRP3 conformational changes secondary to activation or aggregation to ASC. Recruitment of caspase-1 and its activation in the inflammasome appears not to be inhibited if the stimulus is NLRP3-independent and thus 16673-34-0 is not a caspase-1 inhibitor.

From a clinical standpoint, 16673-34-0 represents a completely novel approach in the treatment of AMI. Treatment with 16673-34-0 limits the inflammatory response to initial injury and prevents the second wave of inflammatory injury to the heart. While more and more patients are surviving their first or recurrent AMI, many still develop heart failure within the first year due to the "second wave" and ultimately die prematurely of cardiac death. Inhibiting the NRLP3 inflammasome represents an entirely new approach at reducing cardiac injury during AMI and further damage brought about by the inflammation that can follow, with the intent of preventing both acute and longer term mortality.

The importance of the NRLP3 inflammasome is however in no way limited to the field of cardiology. Genetic mutations in NRLP3 are the pathological basis of autoinflammatory disease called cryopyrin-associated periodic syndromes (Wilson and Cassel. Postgrad Med. 2010; 122:125-133). Activation of the NRLP3 inflammasome and production of IL-1β are considered central in acute and chronic inflammatory and degenerative diseases such as rheumatoid and gouty arthritis, diabetes, atherosclerosis, Alzheimer's disease, and cancer, and glyburide analogs such as 16673-34-0 may also be used to treat these and other NRLP3 inflammasome-associated conditions.

Conclusion

The small molecule 16673-34-0, an analog of glyburide which is free of the cyclohexylurea moiety involved in insulin release, inhibits the formation of the NLRP3 inflammasome in cardiomyocytes in vitro, and ameliorates post-myocardial infarction remodeling and peritonitis in vivo, without affecting glucose levels.

Example 11. Longer Term Effects of Treatment of Acute Reperfused Myocardial Infarction Further studies were carried out to investigate longer term effects of the use of 16673-34-0 in vivo in the prevention and treatment of acute reperfused myocardial infarction, acute non-reperfused myocardial infarction and acute doxorubicin induced non-ischemic myocardial injury.

Figure 9:
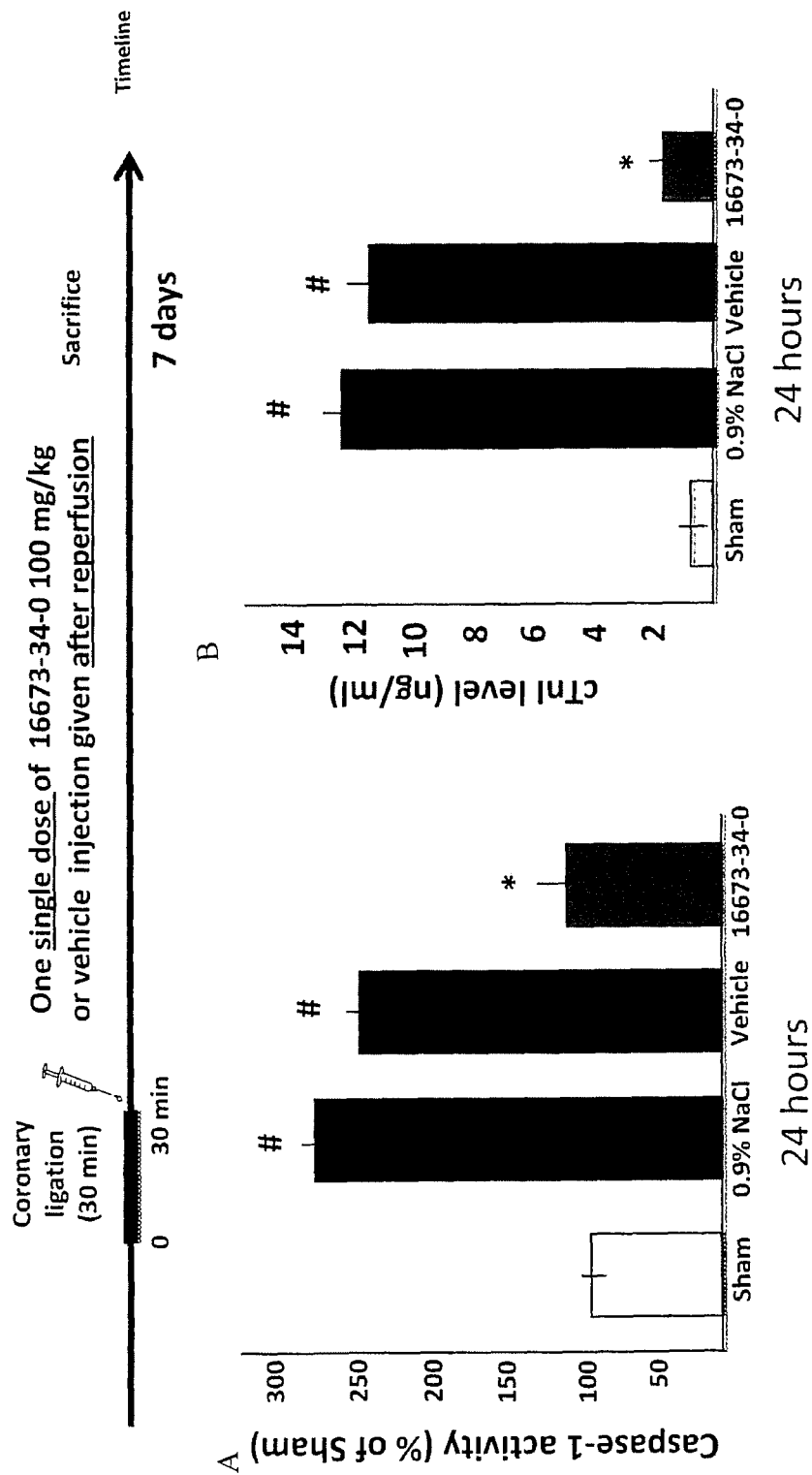
Figure 10:
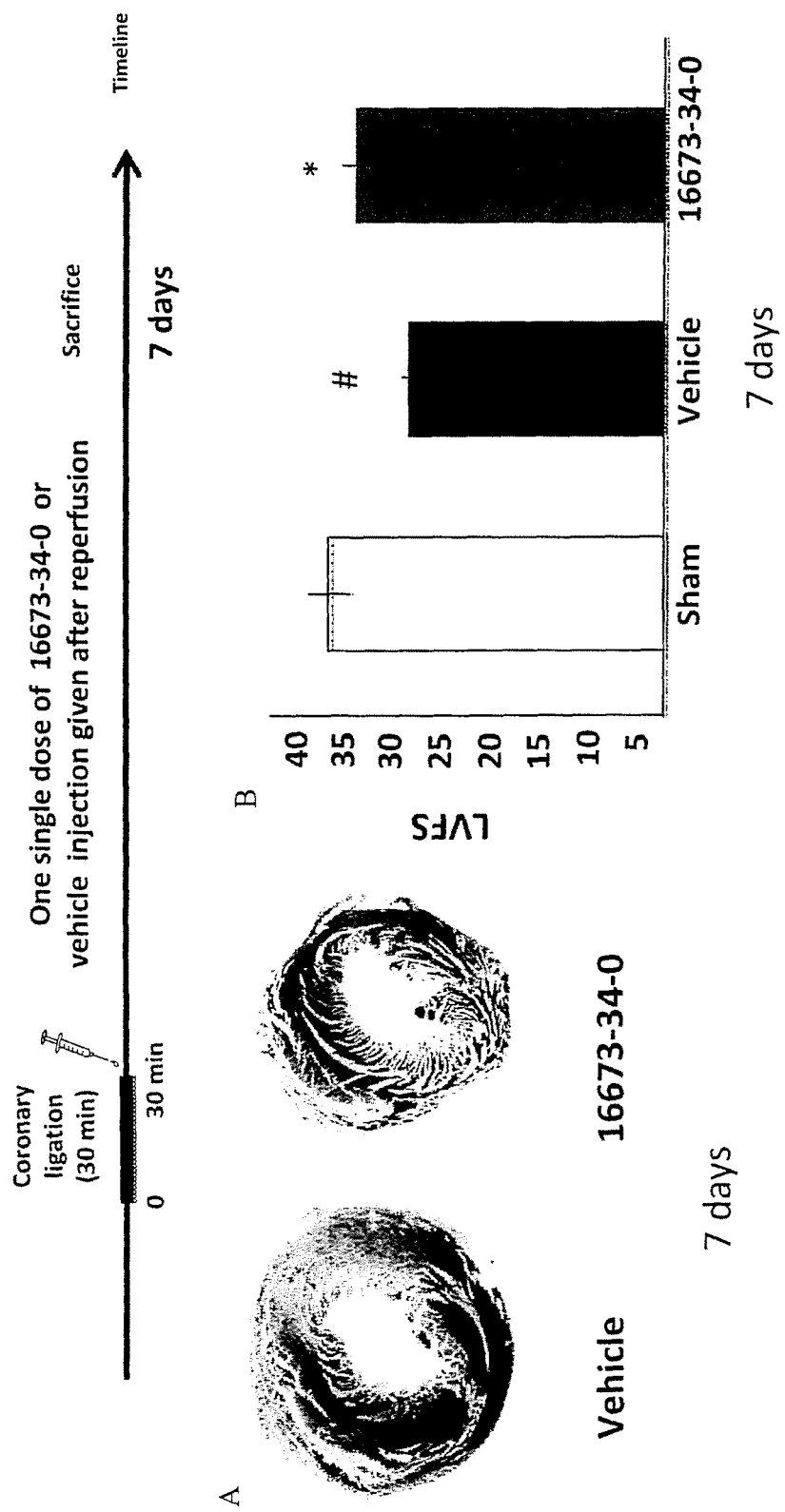

1. Acute reperfused myocardial infarction was induced by coronary ligation as described in Example 1, and a single dose of 100 mg/kg of 16673-34-0 was administered after reperfusion. Caspase-1 activity and cTnI levels were measured at 24 hours (FIGS. 9A and B). The mice were sacrificed at day 7. Left Ventricular Fractional Shorting (LVFS) was measured just prior to sacrifice and showed preserved systolic function in the mice treated with 16673-34-0 (NLRP3 inflammasome inhibitor) and depressed function in the vehicle treated mice (FIG. 10B). After sacrifice, a mid transverse section of the left ventricle was stained for the measurement of the infarct scar showing significantly smaller infarct scare in the treated with 16673-34-0 (NLRP3 inflammasome inhibitor) compared with the vehicle treated mice (FIG. 10A). As can be seen in FIGS. 9 and 10, treatment with the NLRP3 inflammasome inhibitor (indicated as 16673-34-0) provides a strong protection to the heart which results in a smaller infarct and a better systolic function.

Figure 11:
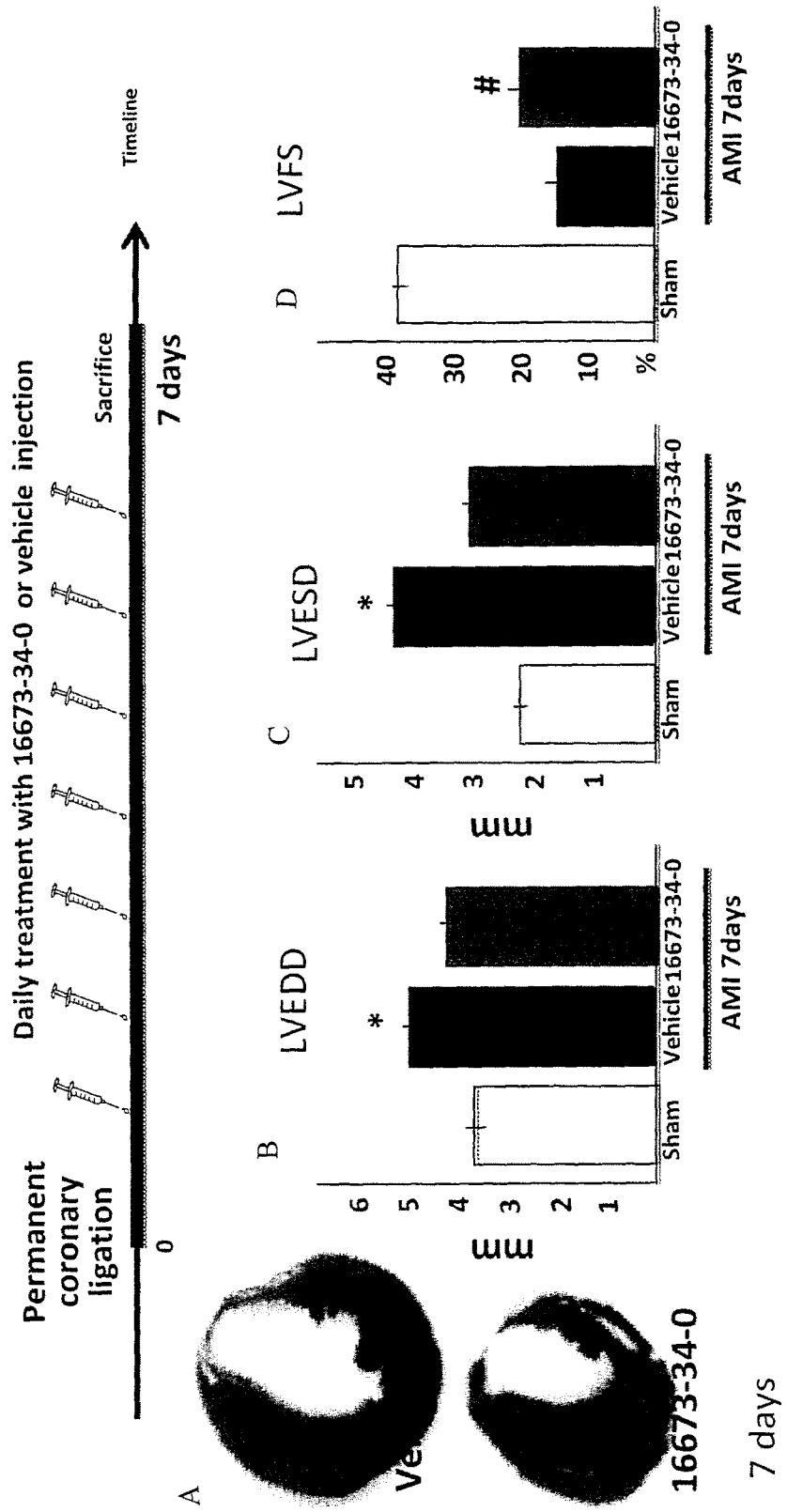

2. Acute non-reperfused myocardial infarction was induced by permanent coronary ligation, and the mice received a daily dose of 100 mg/kg of 16673-34-0 or vehicle. The mice were sacrificed at day 7. Left Ventricular End-Diastolic Diameter (LVEDD), End-Systolic Diameter (LVESD) and Fractional Shortening (LVFS) were measured just prior to sacrifice and showed significantly smaller enlargement and significantly greater systolic function in the mice treated with 16673-34-0 (NLRP3 inflammasome inhibitor) when compared with the vehicle treated mice (FIG. 11B, 11C, 11D). After sacrifice, a mid transverse section of the left ventricle was stained for the measurement of the infarct scar showing significantly smaller ventricular cavity in the treated with 16673-34-0 (NLRP3 inflammasome inhibitor) compared with the vehicle treated mice (FIG. 11A). As can be seen in FIG. 11, treatment with the NLRP3 inflammasome inhibitor (indicated as 16673-34-0) provides a strong protection against cardiac enlargement and systolic dysfunction after large non-reperfused infarct.

Figure 12:
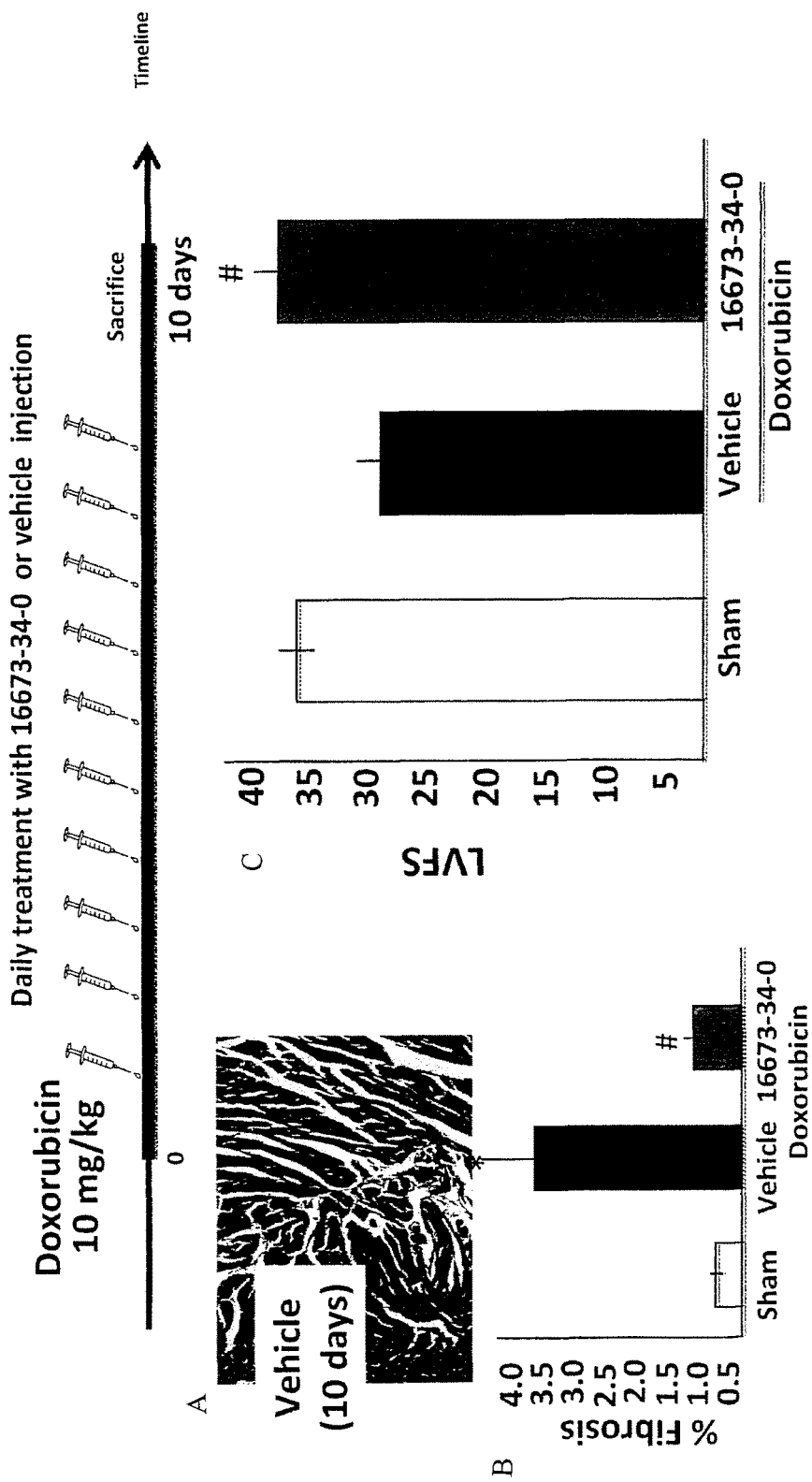

3. Acute non-ischemic myocardial injury was induced by administration of doxorubicin (10 mg/kg). The mice received a daily dose of 100 mg/kg of 16673-34-0 or vehicle and were sacrificed at day 10. The results are presented in FIGS. 12A-C. Left Ventricular Fractional Shortening (LVFS) was measured just prior to sacrifice and showed preserved systolic function in the mice treated with 16673-34-0 (NLRP3 inflammasome inhibitor) and significantly reduced systolic function in the vehicle treated mice (FIG. 12C). After sacrifice, a mid transverse section of the left ventricle was stained for the measurement of the myocardial fibrosis showing significantly less fibrosis in the hearts of the mice treated with 16673-34-0 (NLRP3 inflammasome inhibitor) compared with the vehicle treated mice (FIGS. 12A and 12B). As can be seen in FIG. 12, treatment with the NLRP3 inflammasome inhibitor (indicated as 16673-34-0) provides a strong protection against cardiac injury due to doxorubicin, reflected in less fibrosis and preserved systolic function.

Example 12. Effect of NLRP3 Inhibitor on IL-1β Production in Bone-Marrow Derived Mononuclear Cells (BMDMC) from Wild-Type and NLRP-3 Mutant Mice "NLRP3-mut" is a mouse strain that displays tamoxifen-inducible DNA recombination which leads to expression of a mutant NLRP3 gene that is prone to auto-activation. This strain serves as an animal model of CAPS disease, in which constitutively active NLRP3 due to point-mutations leads to uncontrolled activation of the inflammasome, resulting in severe, often fatal, inflammatory disease.

Briefly, NLRP3-mut and wild-type mice were and treated as follows. Bone marrow was harvested from the long bones. Bone Marrow Derived Mononuclear Cells (BMDMC) were cultured and allowed to differentiate in bone-marrow derived macrophages. Tamoxifen was added to induce DNA recombination and activate the gene mutation: 1 microM 4-oh-tamoxifen (4 hydroxytamoxifen) was added for 42 hours. The NLRP3 inflammasome inhibitor (NLRP3 inh) was added at the same time at a 400 microM concentration; LPS (*E. coli* 0111:B4) 25 ng/ml was added after the 42 hours, and then the supernatant was collected at 48 hours. IL-1β levels were measured with a ELISA-based assay.

The results are depicted in FIG. 13. As can be seen, BMDMC from wild-type mice produce large amounts of IL-1β after stimulation with LPS+ATP, but not after LPS alone (FIG. 13A), whereas the BMDMC from the NLRP3-mut mice, in whom NLRP3 is constitutively active, produce IL-1β after LPS alone (FIG. 13B). However, the NLRP3 inhibitor significantly reduced IL-1β production in bone marrow of both i) wild-type mice after administration of LPS+ATP (FIG. 13A), and NLRP3-mut mice after administration of LPS alone (FIG. 13B).

These results show that the NLRP3 inflammasome inhibitor can be used to treat diseases in which the NLRP3 inflammasome is not constitutively active but rather activated following an insult of sort (FIG. 13A) or it can be used to treat diseases in which the NLRP3 inflammasome is constitutively active such as the Cryopyrin Associated Periodic Syndromes (CAPS) (FIG. 13B).

Example 13. Effect of NLRP3 Inhibitor on IL-1β Production in Cultured Macrophages (J774A.1) after Stimulation with LPS and Monosodium Urate (MSU)

Briefly, FIG. 14 shows that cultured macrophages produce large amounts of IL-1β after stimulation with LPS and MSU. MSU activates the NLRP3 inflammasome, and MSU crystal deposition in the joints is responsible for gout, including acute and chronic gouty arthritis. The macrophages were incubated with LPS for 4 hours as previously described and then MSU was added to the plate to form crystals. The addition of the NRLP3 inflammasome inhibitor (NLRP3 inh) significantly inhibited the production of IL-1β.

These results show that the NLRP3 inflammasome inhibitor can be used to treat gout, gouty arthritis and other diseases in which crystals of MSU or other related crystals activate the NLRP3 inflammasome.

Example 14. Compounds of Formula III ("GA2") and Formula IV (GA3") Reduce Infarct Size in Experimental Acute Myocardial Infarction In Vivo Experimental AMI was induced in mice by transient myocardial ischemia for 30 min followed by 24 hours of reperfusion. Different groups of mice were treated with GA2 (100 mg/kg in 0.1 ml), GA3 (100 mg/kg in 0.1 ml), vehicle DMSO solution (0.1 ml, vehicle), or glyburide (132.5 mg/kg in 0.1 ml) (FIG. 15A), given intraperitoneally at the time of reperfusion. The heart were explanted at 24 hours and processed for the measurement of infarct size using triphenyl tetrazolium chloride (TTC staining). The areas of infarcted tissue, the risk zone, and the whole LV areas are determined by computer morphometry using Image Pro® Plus 6.0 software (Media Cybernetics, Silver Spring, Md.). The results are presented in FIG. 15B, where the infarct size is expressed as % of the risk zone (or area at risk).

As can be seen, we found a significant reduction in infarct size using GA2 or GA3 vs vehicle and vs glyburide, whereas glyburide increased infarct size compared with vehicle. These data show that, although GA2 and GA3 derive from intermediate compounds in the synthesis of glyburide, GA2 and GA3 have a cardioprotective effect that glyburide does not have; and confirm that glyburide actually has a toxic effect on the heart during ischemia-reperfusion.

In an additional experiment we compared GA2 and GA3 with the compound identified as "G1" in the report by Lamkamfi et al. J Cell Biol 2009. The report had shown that the G1 compound inhibited the NLRP3 inflammasome in vitro, yet no data on efficacy in vivo were presented.

As described above, experimental AMI was induced by transient myocardial ischemia for 30 min followed by 24 hours of reperfusion. Different groups of mice were treated with GA2 (100 mg/kg in 0.1 ml), GA3 (100 mg/kg in 0.1 ml), vehicle DMSO solution (0.1 ml, vehicle), or the G1 compound (100 mg/kg in 0.1 ml) (FIG. 16A, given intraperitoneally at the time of reperfusion. The heart were explanted at 24 hours and processed for the measurement of infarct size using triphenyl tetrazolium chloride (TTC staining). The areas of infarcted tissue, the risk zone, and the whole LV areas are determined by computer morphometry using Image Pro® Plus 6.0 software (Media Cybernetics, Silver Spring, Md.), and infarct size is expressed as % of the area at risk.

The results are presented in FIG. 16B. As can be seen, we found a significant reduction in infarct size using GA2 or GA3 vs vehicle and vs the G1 compound, whereas the G1 compound had no effect on infarct size compared with vehicle. These data show that although GA2 and GA3 share some structural characteristics with G1, GA2 and GA3 have a cardioprotective effect in vivo that the G1 compound does not have.

In a further experiment, AMI and reperfusion were performed in mice as described above, and a single dose of GA2 was given i.p either immediately at reperfusion or delayed until after 1 hour of reperfusion. The results are presented in FIG. 17. As can be seen, in both cases, administration of GA2 reduced infarct size.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A compound or a pharmaceutically acceptable salt thereof having the structure

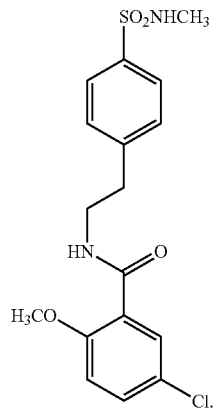

Formula IV

2. A composition comprising a physiologically acceptable carrier and a compound or a pharmaceutically acceptable salt thereof having the structure

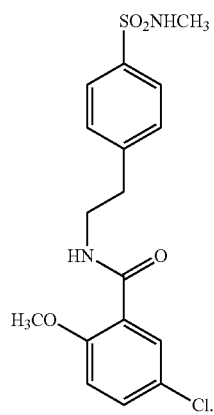

Formula IV

* * * * *